United States Patent
Bennett et al.

(10) Patent No.: US 6,692,960 B2
(45) Date of Patent: Feb. 17, 2004

(54) ANTISENSE MODULATION OF SPHINGOSINE-1-PHOSPHATE LYASE EXPRESSION

(75) Inventors: C. Frank Bennett, Carlsbad, CA (US); Susan M. Freier, San Diego, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 41 days.

(21) Appl. No.: 09/967,669

(22) Filed: Sep. 28, 2001

(65) Prior Publication Data

US 2003/0092650 A1 May 15, 2003

(51) Int. Cl.[7] .................. C07H 21/04; C12Q 1/68; C12N 15/85; C12N 15/86; C12P 19/34
(52) U.S. Cl. .................. 435/375; 435/325; 435/6; 435/91.1; 536/24.3; 536/24.31; 536/24.33; 536/245
(58) Field of Search .................. 435/6, 91.1, 91.3, 435/325, 375; 536/23.1, 23.2, 24.5, 24.3, 24.31, 24.33; 514/44

(56) References Cited

U.S. PATENT DOCUMENTS

| | | | |
|---|---|---|---|
| 5,801,154 A | * | 9/1998 | Baracchini et al. .......... 514/44 |
| 5,959,097 A | * | 9/1999 | Monia et al. |
| 6,040,179 A | * | 3/2000 | Cowsert |
| 6,187,562 B1 | | 2/2001 | Duckworth et al. |

FOREIGN PATENT DOCUMENTS

| | | |
|---|---|---|
| WO | WO 99/16888 | 4/1999 |
| WO | WO 99/38983 | 2/2001 |

OTHER PUBLICATIONS

DW Green et al., Collective Review, "Antisense Oligonucleotides: An Evolving Technology for the Modulation of Gene Expression in Human Disease," Jul. 2000, vol. 191, No. 1, pp. 93–105.*

AD Branch, TIBS 23, Talking Point, "A good antisense molecule is hard to find," Feb. 1988, pp. 45–50.*
N Milner et al., Nature Biotechnology, "Selecting effective antisense reagents on combinatorial oligonucleotide arrays," Jun. 1997, vol. 15, pp. 537–541.*
K-Y Jen et al., Stem Cells, "Suppression of Gene Expression by Targeted Disruption of Messenger RNA: Available Options and Current Strategies," 2000, 18:pp. 307–319.*
S Agrawal et al., Molecular Medicine Today, "Antisense therapeutics: is it as simple as complementary base recognition?," Feb. 2000, vol. 6, pp. 72–81.*
Boumendjel et al., *Synthesis of an inhibitor of sphingosine–1–phosphate lyase*, Tetrahedron Lett., 1994, 35:819–822.
Li et al., *Molecular basis for resistance to the anticancer drug cisplatin in Dictyostelium*, Microbiology, 2000, 146:2219–2227.
Saba et al., *The BST1 gene of Saccharomyces cerevisiae is the sphingosine–1–phosphate lyase*, J. Biol. Chem., 1997, 272:26087–26090.
Spiegel et al., *Functions of a new family of sphingosine–1–phosphate receptors*, Biochim. Biophys. Acta, 2000, 484:107–116.
Van Veldhoven et al., *Human sphingosine–1–phosphate lyase: cDNA cloning, functional expression studies and mapping to chromosome 10q221*, Biochim. Biophys. Acta, 2000, 487:128–134.
Yatomi et al., *Sphingosine 1–phosphate: synthesis and release*, Prostaglandins, 2001, 64:107–122.

* cited by examiner

*Primary Examiner*—Karen Lacourciere
(74) *Attorney, Agent, or Firm*—Licata & Tyrrell P.C.

(57) ABSTRACT

Antisense compounds, compositions and methods are provided for modulating the expression of sphingosine-1-phosphate lyase. The compositions comprise antisense compounds, particularly antisense oligonucleotides, targeted to nucleic acids encoding sphingosine-1-phosphate lyase. Methods of using these compounds for modulation of sphingosine-1-phosphate lyase expression and for treatment of diseases associated with expression of sphingosine-1-phosphate lyase are provided.

14 Claims, No Drawings

SEQUENCE LISTING

```
<160> NUMBER OF SEQ ID NOS: 90

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                               20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
atgcattctg cccccaagga                                               20

<210> SEQ ID NO 3
<211> LENGTH: 5741
<212> TYPE: DNA
<213> ORGANISM: Homo sapiens
<220> FEATURE:

<400> SEQUENCE: 3
```

-continued

| | | | | | |
|---|---|---|---|---|---|
| gcggctgccg | ggcctccaat | ctcggcggcg | gcggcggcaa | caggggagcc | tgggtctcgc | 60
| ggcctgcgag | tccgtcgcgt | gctgagggag | acgcaggagg | tggagccggc | cgggtgctcg | 120
| agggaaggag | actggaagct | ggttccggcg | tgaggagagt | ctgaaaaagg | ggagcgcgga | 180
| gaggaggctg | aagaggaag | atgcctagca | cagaccttct | gatgttgaag | gcctttgagc | 240
| cctacttaga | gattttggaa | gtatactcca | caaaagccaa | gaattatgta | aatggacatt | 300
| gcaccaagta | tgagccctgg | cagctaattg | catggagtgt | cgtgtggacc | ctgctgatag | 360
| tctggggata | tgagtttgtc | ttccagccag | agagtttatg | gtcaaggttt | aaaaagaaat | 420
| gttttaagct | caccaggaag | atgcccatta | ttggtcgtaa | gattcaagac | aagttgaaca | 480
| agaccaagga | tgatattagc | aagaacatgt | cattcctgaa | agtggacaaa | gagtatgtga | 540
| aagctttacc | ctcccagggt | ctgagctcat | ctgctgtttt | ggagaaactt | aaggagtaca | 600
| gctctatgga | cgccttctgg | caagagggga | gagcctctgg | aacagtgtac | agtggggagg | 660
| agaagctcac | tgagctcctt | gtgaaggctt | atggagattt | tgcatggagt | aaccccctgc | 720
| atccagatat | cttcccagga | ctacgcaaga | tagaggcaga | aattgtgagg | atagcttgtt | 780
| ccctgttcaa | tgggggacca | gattcgtgtg | gatgtgtgac | ttctggggga | acagaaagca | 840
| tactgatggc | ctgcaaagca | tatcgggatc | tggcctttga | gaaggggatc | aaaactccag | 900
| aaattgtggc | tccccaaagt | gcccatgctg | catttaacaa | agcagccagt | tactttggga | 960
| tgaagattgt | gcgggtccca | ttgacgaaga | tgatggaggt | ggatgtgcgg | gcaatgagaa | 1020
| gagctatctc | caggaacact | gccatgctcg | tctgttctac | cccacagttt | cctcatggtg | 1080
| taatagatcc | tgtccctgaa | gtggccaagc | tggctgtcaa | atacaaaata | ccccttcatg | 1140
| tcgacgcttg | tctgggaggc | ttcctcatcg | tctttatgga | gaaagcagga | tacccactgg | 1200
| agcacccatt | tgatttccgg | gtgaaaggtg | taaccagcat | ttcagctgac | acccataagt | 1260
| atggctatgc | cccaaaaggc | tcatcattgg | tgttgtatag | tgacaagaag | tacaggaact | 1320
| atcagttctt | cgtcgataca | gattggcagg | gtggcatcta | tgcttcccca | accatcgcag | 1380
| gctcacggcc | tggtggcatt | agcgcagcct | gttgggctgc | cttgatgcac | ttcggtgaga | 1440
| acggctatgt | tgaagctacc | aaacagatca | tcaaaactgc | tcgcttcctc | aagtcagaac | 1500
| tggaaaatat | caaaggcatc | tttgtttttg | ggaatcccca | attgtcagtc | attgctctgg | 1560
| gatcccgtga | ttttgacatc | taccgactat | caaacctgat | gactgctaag | ggtggaact | 1620
| tgaaccagtt | gcagttccca | cccagtattc | atttctgcat | cacattacta | cacgcccgga | 1680
| aacgagtagc | tatacaattc | ctaaaggaca | ttcgagaatc | tgtcactcaa | atcatgaaga | 1740
| atcctaaagc | gaagaccaca | ggaatgggtg | ccatctatgg | catggcccag | acaactgttg | 1800
| acaggaatat | ggttgcagaa | ttgtcctcag | tcttcttgga | cagcttgtac | agcaccgaca | 1860
| ctgtcaccca | gggcagccag | atgaatggtt | ctccaaaacc | ccactgaact | tggaccccttt | 1920
| ctagtctcaa | ggggattcca | gccttcagaa | ggttcttggg | atatggaaca | ggccgtgcac | 1980
| aactttgaca | tctggtcttg | ctccatagag | cacaactcaa | gatagaccat | gagacagctt | 2040
| gagcctcagg | attcttgttc | ttcctcttat | cttccttttg | tggttttttaa | tttgaagacc | 2100
| ccagagaatt | ccattacata | atgattttgc | ccttgttata | aatgttaccc | taggaattgt | 2160
| tttaaccatt | tccttttcta | aactctctag | ctttcaactt | tacttaaaca | ttgtgtggta | 2220
| gctctgacct | gtcctgattc | tttagagaag | ctggggtaca | gtttatgaga | tagctagagc | 2280
| ttctttgtta | tctcaggcag | gaggcgttta | cataacagat | gtttcctcag | ctgggtgtga | 2340
| ggtatactct | aagcaggagg | cttttttcagc | cttctctctc | tttttttttt | tttttttttt | 2400

```
ttgagatgga attttgctct tttgcccagt ctggagtgca gtggcatgat ctcagctcac   2460
tgcaacctcc acccactggg ttcaagcgat tcttctgcct cagcctcccg agtagctggg   2520
attaccggca cccaccacca cgcctggcta attttttcaat tttctttttc agtagagacg  2580
ggttcaccgt gttggccagg ctggtcttga actcctgacc tcaggtgata cccgcccccc   2640
cgcctcagcc tcccaaagtg ctgggattac aggcgtgagc caccgtgcct ggccctgtct   2700
ctcttaagag taggttcatt gtctgtctta gagtcacttc tattgcaact catttctttt   2760
ttccagggca cagatcgacc aagctgccgt tccctattct gcaggacagg actattctag   2820
catacctgct tcgtccaccc aggcagggtt tggggtggtc tcttctgtgc ctgcagtccc   2880
catttgacac ttggttgcca ccatctttgg agattattgt ttggaatgat gcttccattg   2940 gcttttctt gttaccatgg actaggaaga aacatggtt tccaaataat ctgggagctt     3000
ttggccatgg tgccgccttc ctgaattggc agtggtcaga gcacacctga acctatcct    3060 gggctggtga tgagcagaaa tcagaccttt ttctatgctt ttttgaatat cagagtagga   3120
tgaacaccca gattcaaata tgtcaccaaa gttggtggtg gtccttccct gcacccttgc   3180
gttaagccat tatgtaatga aaatgtgttt gcttgaagga acagctcaaa gcaccttcac   3240
aagttgcctt gacttaccct aggtgggtgt gaaagagcac ccgtagcaag gaaaattttc   3300
tctattagtg tgttcttctg cctcttcccc cttgattcag ctttcagagg tactatggca   3360
gttttgcctc aggtgctgaa catttctcag ccctggctaa aagggagcag cacagggaga   3420
gaaacaggat aggaaagcag aatggcgagc agcctatggc ccagggcctg taatcccttc   3480
ccaagactag ctgctcaggg tggtgcaggg acaggaccag accctgcgcc tatttcctgc   3540
cttctttccc ctatagggaa ctctgtaggc tgagccactg tcctgctctt atgacattat   3600
atcttgtgcc tttctcctca gcagtgagca gtgagctact cctggcccag gcctagggg    3660 aaatggatca gtctttgagg tttctatttg gggagggag tacttaagat gagtcaaaag    3720
acactttcct ctgttccatt ccccatctca gggactcctg aatattcagc ctctccaggc   3780
tggtgtcttc tagtttcccc cactgggaat gctggctggg agagccatga ctaccagact   3840
tttcctcagg ctccttggca tgttagtctg aattgttctt gagcactgta ctactgaccc   3900
aacaactgtg actagctggc cacgccattc agggctggtg tggcatttat gtgtgtgtgt   3960
gtgtgtgtgt gttttttcctg tttgcccagc agtgcattgt gggttccaag agtgggtagt  4020
gtgtgtatgt gtgtgtgtca gagggagacc tggcaggcac ctctttgaga gtagctgtgg   4080
tcagagctgt ttggtcagtg cattatgttg aatgaggtcc aggaacccag agccacccag   4140
cagacaccac tgtggcttgc cagctgccaa gatggagaag catgtgcccc tgtagagcgt   4200
ctccccagaa ccagaccccg agccactcgc ttcctctgtg ctgtgacaac attggtgcca   4260
ggggagatgg tgtttttcaa agggacctac tgtagccact ttaatttaca attaagagcc   4320
ttagtttgac ttaacacttt tgtaggcttt tcattgtgta ttttgtgta tgtgtgcata    4380 tagcagctac tctgtagcag aggtgggtag agacacttaa tagtatcatg tcgcatgcag   4440
atgtcacatc ggcctctgca aaaactgtac tgtcttgttt ctgcattaga cttaagtagt   4500
catgtgaata tactgctatg tcacttttaa tattacgagt tttatacttg gaaaatggta   4560
cttgcttctt ttaaatctct gtcttctcta acctcccct tcccatttca atgctcccttt   4620 cctaatttca gcaataatct caaaaagcaa ttaaatagtt aaatgaccct aattgtaatt   4680
actgtggatg gttgcattca tttgattact tgggcacaca cgagatgaca aatggggcag   4740
```

```
tggccatgct tgaatgggct cctggtgaga gattgccccc tggtggtgaa acaatcgtgt    4800
gtgcccactg ataccaagac caatgaaaga gacacagtta agcagcaatc catctcattt    4860
ccaggcactt caataggtcg ctgattggtc cttgcaccag cagtggtagt cgtacctatt    4920
tcagagaggt ctgaaattca ggttcttagt ttgccaggga caggccctat cttatatttt    4980
tttccatctt catcatccac ttctgcttac agtttgctgc ttacaataac ttaatgatgg    5040
attgagttat ctgggtggtc tctagccatc tgggcagtgt ggttctgtct aaccaagggg    5100
cattggcctc aaaccctgca tttggtttag gggctaacag agctcctcag ataatcttca    5160
cacacatgta actgctggag atcttattct attatgaata agaaacgaga agttttttcca   5220 aagtgttagt caggatctga aggctgtcat tcagataacc cagcttttcc ttttggcttt    5280
tagcccattc agactttgcc agagtcaagc caaggattgc ttttttgcta cagttttctg    5340
ccaaatggcc tagttcctga gtacctggaa accagagaga aagaggatcc aggatgtact    5400
tggatgagga ggcctggctt atctaggaag tcgtgtctgg ggtgcttatt gctgctccat    5460
acagctgtac gtcagcccct tggccttctc tgtaggttct tggcagcaat gagcagcttt    5520
cactcagtga cacaagtaat tactgagtcc taatttgata gccaccaact gtacctgggt    5580
aggcaaagtc agattttga gaaccttttt cctgatttga agttttaatt accttatttt    5640
cttttatgct ttcctctgtc ttgtaatctt ttctcttctt aatatccttc cctataattt    5700
caattatttg gattaatttt agaataaacc tatttatttc t                        5741

<210> SEQ ID NO 4
<211> LENGTH: 21
<212> TYPE: DNA
<213> ORGANISM: Artificial Sequence
<220> FEATURE:
<223> OTHER INFORMATION: PCR Primer

<400> SEQUENCE: 4
agtaaccccc tgcatccaga t                                                21

<210> SEQ ID NO 5
<211> LENGTH: 23
<212> TYPE: DNA
<213> ORGANISM: Artificial Sequence
<220> FEATURE:
<223> OTHER INFORMATION: PCR Primer

<400> SEQUENCE: 5
gaacagggaa caagctatcc tca                                              23

<210> SEQ ID NO 6
<211> LENGTH: 28
<212> TYPE: DNA
<213> ORGANISM: Artificial Sequence
<220> FEATURE:
<223> OTHER INFORMATION: PCR Probe

<400> SEQUENCE: 6
tcccaggact acgcaagata gaggcaga                                         28

<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7
```

```
gaaggtgaag gtcggagtc                                              19

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
gaagatggtg atgggatttc                                             20

<210> SEQ ID NO 9
<211> LENGTH: 20
<212> TYPE: DNA
<213> ORGANISM: Artificial Sequence
<220> FEATURE:
<223> OTHER INFORMATION: PCR Probe

<400> SEQUENCE: 9
caagcttccc gttctcagcc                                             20

<210> SEQ ID NO 10
<211> LENGTH: 54945
<212> TYPE: DNA
<213> ORGANISM: Homo sapiens

<400> SEQUENCE: 10 gtacctttc  tgcccatatg aattctctcc tagccattct ccataccacg cagacggatt    60
gttctaaaac acaaatgtga tattgtcagt cccttgactg aaaagacctc aacggctgtt   120
gctctttgga tgaagatcaa aacactgttt cctacaggac tgggaggtct cagacaggag   180
gattgccatc tgcatttgca tttatttaaa aaacaattga actggtgaca ttctgttttct  240 tgatctgggt ggtgctgaac aatggtgttc actatgtcaa tattcatcta gctctacact   300
ttgatttgtg gacttgtctg tacatacaat gtatcccaat tttaaaaaat cttcaaaaca   360
actgaatgag ttgcccaaag ttctgggagt tccttggtcg tattacactt tatgatcttt   420
tagatctctt gaccaatacc atacaactag agatttttt ccccctttct atcttgggag    480
gaaaaagatg gaattaacaa acagaggtga ttcagtgagt tacattgtgg tcacaagata   540
aattatgcac attgcgacaa gaaaaccaca tagtcctata aaattatggg ctgttttat    600 ccagaattat gctggctttc tatttcctgt tgttgattaa gaataaagag ggacctgcct   660 gttgccctg  cctgcagcgc ctagaggaga gagagaagtc atgatcagcc tcatttctgc    720
cccagggact gcattattcc cctttgaagc aacagtgctt cccctagagc ttggtcaagg   780 agagggctg  caggcaaccc ctgtgtctgc cccaagaaaa tgggagttct gagcaacttg    840
ggtgtatgga aaaggaagc  actctccaca gatggctgaa aagcattgtt ggtaacatat    900
gaagcttgag tctaggggta aatgacaagc cctttaagtg ggctctgttt cttggagtgc   960
tgaactgttc ccactgttta acataaagaa ccaaagtagc ccttgcaaag agagtgagaa  1020
taatctctga ctctggcagg ctcttaggac atcataattt taaaattgag agaattttta  1080
aaaatctaga tttctgtctt tccttggaaa attgagatgt tgaactaccc tactatgcta  1140
ttaaaattgc caggtatggt ggctcatgac tgggaggctg aggcgggtgg atcacccaag  1200
gtcaggaatt caagaccagc ctggccaatg tggtaaaacc ccgtctctat taaaaataca  1260
aaaatagcca ggtgtggtga tgtgcatctc taatcccagt tacttgggat tagggcagga  1320
```

-continued

```
gaattgcttg aatctgggag gtggaagttg catgagccaa gatggcgcca ctgcacttta    1380
gactggatga cagagcgaga ctccatctca aaaataaat aaataaataa ataaataaaa    1440
ttgcagtatc catgacatct tgtcctaaac cccatacttt gtgcttccct tacattgctt    1500
tgcttcctct ctttccatag ccccaagcat ctcctaactt accatatagt ttacttattt    1560
attctgttta ttagtctgtc tccttctgct ggaatgtaag ttgcatgagg gcagggccct    1620
ttgttttgct caatgatcca tcccaggtcc tgaatattgc aacctggcat tgaatagttg    1680
tatgcatgtt gaatgaatgt agcctgaagc ctacattccc aatttgtagc agtcacattg    1740
cctgcctggg cccctgaagg catgtgtatt tgccatgcct gccccctactg acctgcatgc    1800 cagcttctgc cttccgtccc cctcaggctt gtttctctgg ccacactggc ctggcctctc    1860
ctgccccaac actggccctc cgcacttgct cagccagaac gctcttcctg cccctctctg    1920
cctggctagc tcctgctcct gctgtgttct cagctcaagc tgtccttgat ccctctgcct    1980
aggtcactcc cccaagcaca gagaatattc tgtccttagt cactgactag aggaaattcc    2040
tttcattcag ttttcagaca taaaaagctc ttcatccctt gtgaattagg gtgccccccc    2100
accccgcccc tggctaccct gacctctgag cttaggatac aggtggtgcc cagcccctct    2160
gagtcaaccc tggaaaccag ttctacaggg ccaggcaagg agcaaccctg gccaagggc     2220 tgaaattacc ccactggtcc tctgtctacc cacgacttat ataaggctgg gcctcttcat    2280
catgtcctat ctgtgtcaac actcaggagg gtggtgagag ggcctggccc cccagggcat    2340
tctggcaaca tgttcatcct tcacagcagg gccaggacaa cactccctg accaagtaac     2400 cacaagacag agggcccttc ctgggcacct ggagacagac agatggagtt accaaacaga    2460
agattctggg aaggggaacc ccagtgggcc aaagagaact ctagactgac agaggtgagg    2520
aacagcttcc cctctctacc caattttgag atgaggaaat tgaagcccag agagagctaa    2580
tggtgcatcc aaagccccac agcacagggt cccagcagcc ccacaagaac ccacaagctt    2640
cactgtgttt tctgggtctg ggcttctggg gctggaatgt caggaattct aggttctgcc    2700
cccattagct gcaagaccaa gacttagaaa gagatgagaa tggttagaat gttgcagctc    2760
ttatccggga atgtacaaaa tacagatgac tgggcctcac acctcattcc ctccatctgc    2820
aggagggccc tgacatgtgg atttttgaaag gctccttgga gatgctgact atccatgcta    2880
gatgggcacc tggatgatgt ttaagtccct tctagcttga caaatcctca gctgtagata    2940
ttaaaatgct gcttgtgctg gagtgtatcc ctgtcatcag tccacaagag aagctctcac    3000
tggggcagct gggctcccta gggagcaccc tggaaattaa aaaaaaaaa aacttttggt     3060 tgtcataatg atgaggctgg tgcttctggc attcagtgag gggaatactg cagtccctgg    3120
ggcagaaata aggcccatga tgactttttct ctctccccca ggtgctgcag gcaggggcaa    3180
caggcaggtc cctctttgtt cttagtgagg gatgcatccc atcacattga agaattgtcc    3240
tgagtcctgt acatcttttg aatgtactgt cagaatattc atagaggtga aaagctagtt    3300
cataggcaca tgagccataa tcaacttcac tttacatgta cgtttaaaaa aaaaaaacac    3360
cctggtgcag tggctcatgt ctgtaatcct gaagcgggtg gatcacctaa ggtcaggagt    3420
tcgagaccag cctggccaac atggtgaaac cttgtctcta ctaaaaatac aaaaattagc    3480
ctggtgtggt ggcaggcgcc tgtaatccca gctactcggg ggactgggc aagagaatcg     3540 cttgaaccgg ggagacagag gttgcagtga ccgagattg tgccactgca ctccagcctg     3600
ggcgacagag tgagactctg tctcaaacaa caacaacaac aacaacaaca acaacaacaa    3660
caacaaaaaa gaacacatga ttttattgca caacctacct ggagtacaac taccatgttg    3720
```

-continued

```
agagctgtgt gtaaattgtc ctgcattttg tctgaaacgt tatcgacctt aagccacagt    3780
tttgtaaaat cacatcatcc atggcaatgc tgctcacata gtaattgagt cactaagaca    3840
ctacctctat actggtctgc atctgcagct ttcctatcca tgatgattgt atctaattct    3900
atgaatagcc taatttagtc cttatgtcaa aatgtcaaat ataaagaaag cagtgacagc    3960
actattcaat taaatattgc cttcctgtaa tgcaaacata tccattgtaa gtccatgcct    4020
ctgccaactt catgtatgat tttatcgtga cattcccttt taaaattata gtgctatatt    4080
gatttcaaga tagtaaaaga gagttacaaa acaatatttg ttataaacag gggtgttgga    4140
tctggttggt ttaggactta ctgatctaca agcaataaaa cctgcaggaa aacagtagat    4200
ctgtagctct cagacaagcc ttgcaaaggt ctagcatgcc ctagagaggg caaggggcac    4260
gttggaagga ctaatcaact tgttaggatc aggtcctgat ggggatcgaa accagcttcc    4320
agcaacaatg tgagggggct aggctgggct tagtcaatca cacggctcag attggaatct    4380
tatttgagta caccctggat gtatgcggag ggtgttagac caataattct tggccgggcg    4440
cggtggctca cacctgtaat cccagcactt tgggaggcta aggtgggaga atcactggag    4500
cccaggagca gcctaggcaa catagtgagg cattgtcttt ataaattaat aataataata    4560
atagtaataa ttattgagtg cttatggtgg atcaggcctc atatgtgatg ggcacacaca    4620
tacatctctt acaattgcca cagcagtctt agggtagttg ttaattcttg ctttacaaag    4680
gaggaagccc aggcttggac agttacaaca acttgctgga ggccacacaa tgattcctgg    4740
gtagaaagct gtctccctgc cttcaaagct attttgaggc cacacaatga ttcctgggta    4800
gagacctgtc tccctgcctt caaagctatt tgtcaaagg aagtttatat ttattcagtg    4860
tttgagaaac agctgctctc agtttttaat gttttgctag gagtgactgt gcagcctgga    4920
tagcaacaat ggtgggtgta ttagtccgtt tcacactgtt attaagaact ccctgagac    4980 tggggcattt ataaaggaaa gaggtttaac tgactcacag ttccacacgg cttggggagg    5040
gctcagaaga cttacaatca tggcggatgg tgaaggggaa gtaagcccct tcttcacaag    5100
gcagcagcag agagaagaac gaaggaagaa cttccagaca ctcataaaac catcaaatct    5160
catgagaatc actcagtgcc atgagaacag catgggggaa accacccca tgatccaatc    5220 accctccctc cctcgacaca tgggaattat gatttgagat gagatttggg tggggacaca    5280
gagtcaaacc ctatcagtgg gcttctttac gaaagatgag gtttccttgg gaaataactc    5340
ttggctctct gagggcttgg ccactctgac tttgatcaaa ctggcaactg gggtatgtac    5400
ctgagtgagg tcagggggcc catgataact cggtgacttg ctgccccttg ctcactccag    5460
ttggcaatgt cggggcattt ggtccctgct gtggggctc ccatgtctgt ctggcccttg    5520
gcctctcctc cctggtggc cagctctgct gtgatcagct gagcctgctg ctggagctat    5580
gtgctggttt cctgcctctt cttgggcatt ctgggctcta ggaactgttt gttggtttcc    5640
tgtgggccat tcctttccag gatgggccta gaggctgcaa ccctcctaag atctgcccac    5700 accctgtcc tgaggtaagc ttctcaagaa ggtccccggc tgagcaaggg gtgtcaggag    5760
caagaaagga ggcaggagag tgtgtgcgcc tgctttttag agtgggagtg tgcactcatg    5820
catgagtggg aggctgtcat taacttggcc atggatggct gccattttaa gcagaaccag    5880
atttgctggc atgaattgtt taaatgatgg caggcacaag cactgcaggg agatcctcct    5940
agcctaaatt aaagaagcca cagagggaaa aaatcccaga ccatcttgct ccacacctcc    6000
ctcccccgtc ccaagccttc cgtcatctgc gggaatttca gtgcctcact gacacctgaa    6060
```

```
tgacaatctt ttgtcatcct ggaaggcacc atgatggtac caaggacaaa ctggggagca      6120
ttggttccct ccccagcccc aaacaaacac gttcttcatc agcctcctta agccatccca      6180
aacaacccac acgcttaata caactatcgt gccttctatc cgggcaaagt gccatgtgtc      6240
tgtagacaca gctactcagg aggctgagac aggaggatcg ctcgagccca ggagtttgag      6300
gctgtagtga gctatgataa tggctgtaaa tagccactac actccagcct gggcaacatt      6360
atggagacca tgtttctaaa taagcaaaca aaaattgtgc tttctctgca aacagagtgt      6420
ctagggaagt gcttttttact ttcttgtgca ttaagatcat ctggggacct tgttaagctg      6480
tagattctga ttcaggaggt ctggagtggg gccccaagaa cctgtattta taacaagctc      6540
tcaggtaaag ccaatgctgc tctcagggaa accacacttt cagaatggaa gttccagata      6600
gccctcctct gcctctgacc agccagctat gtgcctgcta acgtcattct gctgtcagag      6660
ggagtgtggg gtaggagagc agggtggtct gaagtctttc tctctctctt tctctctctc      6720
tctctctctc tctctctcac acacacacac acacacacac acacacacac acacacacac      6780
acagggcttc atcggctcag agagttgcaa acccagaccc atgttctagg ctgggctctg      6840
ccaggaactg ctaggagtcg catctctctc tggacctcag tttcttcacg tgtatttgtg      6900
tattctctgg ggtggagctg gcgaatagct ggagacccct ctagctctac catttttttga     6960 ttctaattaa ccaaaaagga tattcgaggt ccccgctaca aattctgaac ccttggcttc      7020
ccctccaaac tcccacacaa actccacccc atcctgcctg tgtgtctttg ggaggatcat      7080
ttccttcttt ggtcttggtg tccttgttta caggttgagg gatgataaga gtcacctgat      7140
ctgggcaagt caggccataa ataaggcttg tatgtaaagg tgcctagcat agttcttggc      7200
aaagcaagga tcagtcgata tgattgcatt ggtttgtgca tctgggaaga atgagcagac      7260
tgcatactgt gtgttagggt gtagggagga atcagacgtg accctgccct ctagtcatct      7320
gggtgcacag attctagatt aaaggatgtg ggggtggtaa ctaacaagga gatggagagg      7380
aggtgtgcag ttcctggggg atctgatgaa gaattaaagg agaagggtag gagatggaga      7440
atgggaaggc atacctgaaa ccctaaagca actcttgatg agtaggcatt ggcaggaggc      7500
cccagaacat tttctgaccc tcaaacactg agaatgcatg tctgctgggg aatagtagtg      7560 aggggggctaa gggtatgggg gtgttcatgc ctgagtcagg ggctctggat ggtagaaatg      7620
tctgggagtt ctgacggaat gggggtgagg aggcctaaag ataacctgtt catagtctttt    7680 cagggcctta accattatgg ctggggaagt gggaagtgcc gatggggtat gcagaggagg      7740
gcagctgtga tagtacattt catcctgaaa gcactacatg tggataatga cggtagtgat      7800
gatgccctaa ttttagtgtc atggcaacat tttccaaggg gatggaattg ggtaccctca      7860
ttagtgtcat ttttgtttga gagatttcaa gagtctatct aggtgtcatt ttaaaatcta      7920
ttgaaaaaaa atcttgaatg caggtcactg accagttggt tccatgtaac tgcactgcct      7980
tctgctacca ctaaagcaat gttatgacaa catggacaag tcatgggaaa cctatgtgag      8040 acttagttt ttcttttttct ttttggagtt gggggtctca ctatgttgct caggctgatc      8100
tagagctcct gggctcagac aaccctcccg cctcagcatc cccaagtgcc gggattaccg      8160
atgtaagcca ctgcacccag ctgagactta gttttttcat ctggaaatga aggcgacctt      8220
tgtgatccca gtgggcccctt gcacttgtgt ataaggtgat tcccagcact gctcatgaaa      8280
gtagtgatgg cagagtagcc tctgctctcc attttatttt tggggtgggg gggcagtggt      8340
ggaggggagg atgaggatga tatttccatt aaataagttt ccttgttgct tttcttcagg      8400
caccactgac ctcgatggaa aaatgaagtc cctggcccag gaaagagacc caactctgtg      8460
```

-continued

```
gctgttttgg attagtttgt acaatgccct gcagacctac tctctcagga ggctccaagt    8520
gaccaaatgt gacaagaaag ttttttgtcc aaggcagttt ggaagagaag ttggtgaccg    8580
tcgggatacc acagccgccc caggacggcc tggttgagac attcactgga gggtctgggt    8640
gcagcccgct gcctggccgg taggcggcgc gcacaggccg tggggcccgg gtctgggcgt    8700
gcgcgcggct ggtagcagcg gggccgcgca cgccaggtc cgggagccgg gccggtgccc    8760
ccggagccat ttccgggagg ggcgaggccg gcggctgccg ggcctccaat ctcggcggcg    8820
gcggcggcaa caggggagcc tgggtctcgc ggcctgcgag tccgtcgcgt gctgagggag    8880
acgcaggagg tggagccggc cgggtgctcg agggaaggag actggaagct ggttccggcg    8940
tgaggaggtg gaggggccgc cgcgggctcc gggggcggt gagggtcggg acggaggcgc    9000
cgcggggtga ggagaggaca ggggccgggt gggccgaggg cgggcagagg cggcggggcg    9060
gctgcgcccg gggcggggc gggggccggg ctgaaggcgt gggcaccagc cgctgaggtc    9120
caagcaagtg gacggcgggc gggcgcgggg ccgcggtggg gcgggtctgg agcccacgcc    9180
tgccgcgggg taggcatggg cggccaggat ttgctggtcc tccgacggga ggggtgacaa    9240
cgagagcgag gccgtgctga ttctgaaggg agtgcggagg aggcaggacc ctggtagcct    9300
cggcaccttc agcccgggtt aggtggcctg ggctgggctc cccacccga tcgcgcgcag    9360 acggggcgtt tccctagtt tccacctggg tggaatgctt tgtgggagtc tgggtctgga    9420
ttagtttcat cagctgtggg agggaaacct agttgcagca ggattttgat tcgctggtct    9480
ggggtgctag gggtggactg tgatatctgg gaatgaaatc tgagccttca aggagggag    9540 agaaccataa cttggctgct ctggcgaatc taggcgggct ggcgagacag tttaaagctc    9600
tagaagtaaa caaacctggt tccctttttac agagtctgaa aaggggagc gcggagagga    9660 ggctggaaga ggaagatgcc tagcacagac cttctgatgt tggtgagcct tttgcagaca    9720
tcctcctggt tccaaggcat ttgtctccgt tttttagtc caaaggatcc cagtgtgtag    9780
atttcacctc tgatgcttgc ttttggtagc tgagcgtttt gccaccttt attttgtttt    9840 gttttgtttt gttttttttgg agacggagtc tcactctgtt gcccagactg gggtgcagtg    9900
gcatgatctc ggctcaccgc cacctctgcc tcctgggttc aagcgattct cctgcctcag    9960
cctcctgagt agctgggatt acaggcgcac gccaccacgc ccggctaatt tttgtatttt   10020
tagtagagac ggggttctcc atgttggcca ggctggcctt gaactcctga cctgtggtga   10080
tccacccgcc ttggcctccc gaagtgctgg gattccaggc gtgagccacc gcgcctggcc   10140
aaccaccttt tattttggat gaatgatcag gatgaataaa tagctgaatt aaatacatca   10200
atacagtata tgtagaactt aaattattga agaatctttt tcaaaattat tattattttt   10260
tttaaatgag acaaggtctt gctatgttcc tcagaccgga gtgcagtggc tatttacagg   10320
cataatcata gctcactgta gcctggaact cccacttcaa gtgatcctct tgcttcagcc   10380
tctggagtag ctaggactag gagcacaggt cacctctcct ggctttcttt ttcataattc   10440
ttgcagtttt aatccctccc ttcccgtact accagagcag ttttgaaacc tctattatta   10500
cgttttatca gggtctgcca tatactagtt tatctgagtg tttgtcttcc agattagagt   10560
tatggttcct cgacaggcag ataatcatgt cttctttgtt tagagatgaa taaacaccta   10620
gcatggtgct ctgaatatag tatgtgctta acaaatgctt gttggattga accagtatga   10680
atttaagttc ttttgttgga cagagaggta tgcctgcttt agagctgttt cctctcctcc   10740
tgagatcttt ctgtgctgtt ttactgagca gggaagaata gcgttgctaa atgcatgttt   10800
```

```
accaaaatga cattttattt ttgggacttt tatgattcct tatggacttc ttagtgtgag    10860
aattatggag agtttatagc tttgaaatgg tggtatagaa aaagtgtccg ggtttagttt    10920
tttttgtttc gttttgtttt gttttgtttg tttgttttg agatggagtt tagctcttgt    10980
ctcccaggct ggagtgcaat ggcacaatct cagctcattg caacctttgc ctcccgggtt    11040
caagcgattc tcctgcctca gcctcccggg tagctgggat tataggtgca caccaccatg    11100
cctgggtaat ttttgttttt taatagagat ggggtttcgc cgtgttagcc aggctggtct    11160
caaactccta acctcaggtg atccacctgc cttggtctcc caaagtgctg ggattactta    11220
caggcgtgag ccgccgtgtc cagccaagtt tgtttgtttg tttgttttg tcacttctct    11280 gagtgcaaaa tcagtgcttt aaaacaatt catttctctc tctttatctc actatcccag    11340
agggtgggtt ggcgtcactg ggaaactggc aaaaactggt agtgagattt ccttatactg    11400
ggtgctgaca tcgtagtggc ataacctgta aggtctgcag gggggctaaa gaagagagaa    11460
actaagtttt gatccattgt gatttgaggc agggatctag gataattta ggttgtatgt    11520 gagagacata gatgaatact taggttatcc gcagatccca atgaaaagtt catctaaaat    11580
agtatcttgc cccaaatttc atggattttt cagtttaat taatacccctt atataactta    11640 aaattcttat tcaaagacca ttatgttaga aatactggaa actataagta agcaaaagga    11700 aagggattt gttaatctcc cctatctcct acatccccctt cattcgcctc taccccgtgc    11760
agtaatttat cacccagaaa taaccgctgt gagcatcttg gatggttaat gcagagtgac    11820
ttgtagcaat tgacagtttc tgtttatcct cttacgaag gatatgttta tgtaaattat    11880
aggttcttat atgtaagata tttcccccatg cacagagata tggttattac ttatagggcc    11940
tatgcattta ctttaacaga acaatgactg ctttttactcg gaatattaac tttggaatca    12000
gttttctttt gaggtatttc tctagctgtt gccaccacct ttcacctcct cacctgttaa    12060
tttagaatgt ttaggagtgt tgctttgctt gttgctgtaa ggaattaatc cacatagatg    12120
cgagtggccc taggcagtca tcactttctg aagacaacat acatgttgca tgaagtgctt    12180
tcactggaaa agttgtcatt cattccttga ctgtaatgta taatactatt tggaactaac    12240
tggtaaagaa ccaataacca tggctgggtt ttcagtggca cactaaccca tcattctatg    12300
aggtgtttct caagctactt tatatgatat gtaaaacatg ttcttggccc tccacctggg    12360
aagaaaggac ctaagtgaat aaaaaaataa cctcagtgca gtgcagcatc tcagaattag    12420
aaatagtctt agaagtcatg ggatgcagct ttttttttt ttttttttt gagacaaggt    12480 ctcactctga tgcccaggct ggagtgcagt ggcatgatct cagcttactg catcctcaat    12540
ctctgaggct cagatgatcc ttccacctca gcctcctgag tagctgggac gacaggcaca    12600
tgccaccatg cccggctgat ttttgtattt attttttgtt tcagcccccgt ggtgaagact    12660 tgagggttag atttcaacat atgaattttt gggggatgta acattcagt ccattgcagg    12720 tataaatgtt ttcaacaagc atttgttgag tatctgtcct ttttctaagc tttcatgttc    12780
ctactagaac actggatgtg gatatccaat aggaatatat ttaagtcagt atcattatct    12840
ttttctcaaa acatcttcta cctttttttac cttcccttcc tcttctagtc ttaccatagt    12900
taatactgat attaactgtt aacatcatag ttaaccagtc tgtcgaactt gaacttgaaa    12960 atttttgaatg atctataccc acacccgaaa aaattactca catacttaaa aatccatgcc    13020
ttttgttttg ttttattgct gttgtttgta atttacttat ttttacctga tactatgttc    13080
tggaaatttt tctacgtagt tcatgtagat ctgtcttctt cttaatgttt catggtatgg    13140
gtacataaaa tgcacgtatt atagtttatt taaccattct tctgtgggtg gacatttaca    13200
```

```
ttattttttc cctttgtta gagaatactg aaatgaatat ccttgaacat gtttatttgt   13260
atacatgtgc aaagtatgca gatgccaaaa agtgagattg ctaggtcaaa acgaacatgc   13320
gtttaaaatg ttgatagata ccaacaaatt gctttacaaa agttcctatc agtttgtata   13380
tcagtttttc taagtccttt ttaaacatgg actggattag cccgttcttg cattgttgtt   13440
aagaaatacc tgagtctggg taatttataa agaaagagg gttaattggc tcatggttct   13500
gcatatttgt acaaacatgg cttcaacatc tgcttccggt gagacctcag gaagcttaca   13560
atcatggcgg aaggcaaaac ttgagcaggc acgtcacatg gcaagagtga gagcaagaaa   13620
gagagtgggg ggaggtccta ggcttataaa caaccggatc tcacctgaac taactgagca   13680
agaactcatt catgaaagat gcaccccgt gatccagtca tctcccacca gacctcatct   13740
ccaatgtcgg gaatcacatt tcaacatgag atttggagga taggcatcca aaccatatca   13800
tggacctagc atacttctcc cagcctcacg tctctgattt aagtgttcac tcatttactt   13860
gggcactgtt acttgggcac tgtcagcccc tgtccatgtt tgtattcagt ataaattgtg   13920
tgccgggcac tctgccacat gttggggatt tagtactgga tgagacagaa atggtccctg   13980
ccatcatgta gcttacactt tgccacatag aacttttgcc atatgcagac tctttttatg   14040
catttgcagc tactatcctc tcttctggt atgactttt tccttttaac ttttctacct   14100
agagaatttt ctttcatcct tttaaccagc ttaaattttg ccctctgtca ttatctttat   14160
cccttcagag ttagatagtc cttcctcagt gctccatctt ggcactcata tgcttttgt   14220 ggctattccc ctgagaagtt ttcgtgattt gtttgtatat gtatgtgcct gtgtgtgtgt   14280
gtgtgtgtgg acacacatct acatcttgca tattagattg taaactcagt atagacttgg   14340
aactatgata tgtacctgaa cacttcccca gcttactgcc ttcaaccctg gagatgctta   14400
atcaatgttg attaagtgaa tgaatagtaa actataaaat gaccttagtt tgtacagggc   14460
attgtagggg attgtagata tgaatagaac tggtctgtct tcaagaactt aaccatatag   14520
tcagggagat aagaaacaga tgagtagact gcaaggcagg ttgtgataag ctctgtatag   14580
gacttatcaa aaatgagtac tggaggagaa tttaaaggga gagaggaatt ctcgtgaatg   14640
agatactctg gtaagtttac agaggacagg ttttttcttg ctcgtaccag gtgttgtgag   14700
gaatacacat gatggtaaga tatggttgct gactgagaga ttatagtcaa gtaaggcctt   14760
agagcaggca ttggtaaatt gtggcctgca agccaaatct ggctcttgcc tgcttttata   14820
tggtccttgt gctaagaatg attttttacat tttaaaaatt gttaaagaat attttatgaa   14880
catgaaaatt atatgaaatt caagttttgg tgtctgtaat tacattgtgt tggaacacag   14940
ccatgttcct ttgtttacac aataactgac tatatttgta ctccagcagc agagaggagt   15000
agttgtaaag gagaatgttt gctttgcaac acttaaaata taaataatt tagtatcaag   15060 ctcattacag aaccagtttg ctgactactg gggtagagaa taggaaagat tcaaatagag   15120
aagagaaatg acattgatat tgggggtatt agtgtgagtt aagagagtgg gacagtgatt   15180
ctagcagtca tatagaaatt ttagggctga agtgacgatc tagcttaacc ctcttactgt   15240
ataaaatagg cacaagattg aaaatagtct caaagtccac tagctgttaa gtggcagtgg   15300
agtgctgctg gagtgactgg tacagaagcc ttgagggctg tagatgataa taagattatt   15360
gctgaagaag ggcaagatcc ggaatgacct tgcccttgaa aaatgagagt tgaagtacaa   15420
actaagaaca gacttctttt ctctctctaa atgtaatgtt tttatttttc acttgtatt   15480 ctagaaggcc tttgagccct acttagagat tttggaagta tactccacaa aagccaagaa   15540
```

-continued

```
ttatgtaaat ggacattgca ccaagtatga gccctggcag ctaattgcat ggagtgtcgt      15600
gtggaccctg ctgatagtct ggggatatga gtttgtcttc cagccagaga gtaagtatgc      15660
tgtctcctct gtaaaggtat agtggtgtgt cactagcctc aaactaattg ctgagagata      15720
ggactaattt attgccttt ggttgttttt ttgtttgttt gtttgttttt gagacggagt      15780
ctccatctgt tgctaggctg gagtgcactg gcctgatctt ggctcactgc aacctctgcc      15840
tcccaggttc aagtgattct cctacctcgg cctcccgagt agctgggact acaggcacac      15900
gccaccacgc ccagctaatt tttgtatttt tagtggagat ggggtttcac catgttggtc      15960
aggatggtct tgatctcttg acctcgtgat ccacccacct cggcctccca aagtgctggg      16020
attacaagcg tgagccaccg tgcccggccc tggtttggtt cttatttta aaatctgttt      16080 aaatgtaaag cagtactttg tcttctgatt ggtcaagtta taacaggact cttgtataac      16140
taatactcct tacattgatt ttttttggat ttgtagttca cgtaaaaacg cctcagaatt      16200
agtcattgta aggatccaca gaaatctcag tatggtttaa acctttggta ccagtttctt      16260
ccctagaaca taattatgtc acctggagtt cccagagcag gaatttattg ctttcatttt      16320
gtgctatcct tttcagtaaa gattaggtga aattggaaca gcacttacat ggtgaccatt      16380
tgagtgcttg ctatgtgcca ggcactgcca tcaggctgtg gggatatctg cacaagtagt      16440
acaggatctc tctcctcttg gagttgaact ggtatcaggg gatcgtatac tttgagcttc      16500
ctagaagtga ctcagtgcca gatcaacatg gggaagaaga ggccacttct cagggtgcag      16560
aagatgagca gtctcagtga tctgcttctg aatcttccac ctttgcttag gattaagccc      16620
ctctcctgcc cacccacctt tttcccgcct agaaacctgg ttgtgtgtta ccttcttatg      16680
agttattttc ctctgcagtc tgtgcttggt gagtgttgtt agtacctaaa cacaagtagt      16740
ggatttggtg ctggatgttc tataacactc ccctgcacct tttccccact cttagtaggg      16800
tatgggagtt aacttccttg ggataagaaa acagtaacat tgaagataat cattagctgt      16860
ttctcatttg cttgaaattt ccccaccact ttgcttccct gataacacct gtttaaaagg      16920
gctctttaat gtgttttttc tgcttttctt ctcttgttca aggaaagtca atttagaagc      16980
cagattccat ttttatctct ttaccctgca aatagcttct tagccattta tggcgcagta      17040
aacattgcaa aacctgacaa ccaagaagca agttccaact gcttagagtt tttaaattaa      17100
agtggaaatg agacctgact ctcctgtgta aatctgtagc tcactccagc tttaaaaacc      17160
ttgtcctcag ttgctgctcc tagtccttgc aagattttct gataaactct aagaaattag      17220
actggccggc ccttccgctg catctgctca atggtttgga tatggatgta gcttgtgtcc      17280
ttctgctctt gcttattcct ttcctaggaa gtattcaatt cagtgagtaa ggggcccatt      17340
tcagaggatt ctgagggta gcaagaaata tactttcttt ttatttttta acttttcatt      17400
aaaaaaaaaa tcagtctctg cttatccttc tattataata aaatatatac aacataaaat      17460
ttaccacttt aaccattttt aagtgtacag ttagtcctgt ggcagtaagt acgttacat      17520 tattgtacag gcatcactat taccagaact ttttcatcac cccactggaa ctccatttta      17580
ataaacatca aataataact gcccattact ctctcccgca tccctggaa accaccattt      17640 attgtatcgc cttgttttac aaatgtacta caattcaaag gtggtacatt tatgaaataa      17700
ggctaagctt agagatctga gatttatatt ttacttgcta tgattaatat taattttagg      17760
tattcttttt aaaacaaatt ttaaaattaa ttggcaaata acattgtttt atatttatca      17820
tgtacaacat atgttttgaa atatgtatac attgtgaaat gggtaaattg agctaattaa      17880
catgcattac ctcccatatt tttcttttt tgtggttagg tatttacttc tgttttcagt      17940
```

```
tctgcagctc actatgccat acattttgct tagctaatag tagagacaca gccatcttag    18000
gttctgatac ttatctgctt ttagtggtca aaaaggaata tgctggcctc tgagaggcca    18060
attttccatg agaaaattgt tagtcgtagt atactgatga gatatgccat ctaaatcctt    18120
gtgggctgaa ctccaagcca tttgaggttt ttttttttgtt ttttgttttt tgttttgag    18180 acggagtctc actctgtcac ccaggctgga gttcagtggc atgatcttgg ctcactgcaa    18240
cctctgcctc ccgggttcaa gcaattctcc ctgcctcagc tcatgagta gctgggatta    18300 taggtgccca ctatcacgcc tgcctaattt ttgtatttt agtagagatg gggtttcgcc    18360
atgttggcca ggctggtttt gaactcctga cctcaggtga tccgcccacc tcaacctccc    18420
aaagtgctga gattacaggc tgaagcccca tgcccagctg agttattttg tttctaaaga    18480
tacaaaacaa aagcagtaca tattcactat ggaaaagttg gacaatatgg gtatataata    18540
agaacaaaat taaaatctta ctactgaagg ataccactat tgtatttctc tgtttctata    18600
tctgaatcca gtttgaacca tacaaaatgt aattttgtaa aaaaaaaatc gtcaaatgtt    18660
gacaatttta tacaatttag cacatacaca cacagcacac tttcatttgg taatttccaa    18720
cttgaatttt agacacagat aagaatgtct tccctccaga gatcagggat aattttgata    18780
gaatattcat ttttttttagc acttgctcac ttgccatgtg ttgctgaaca atcaagttat    18840
ttttagttac actgcactaa aggagtctga agtctggact agtgatgaat ttgctgatc    18900 ttccaacact gaatccctct tgagggaaga gagtatttct ggaacaaagg atggagcctg    18960
gggtagagga gaagtgggca gcggcatgaa ctgtgctggg gttagcagcc tcttccttaa    19020
ttctgcctct gtgattatca gctcacagtt tattactttt actttaatgc tgattttaac    19080
tgtgggttgt ccataattca tcaacagaaa tcagctttat gtcatggagg aaatgataaa    19140
ctctcagttt cttgttgtgt caccttgggt gacacccctta agctctctta gcccatttcc    19200
ttgcaataaa atggacatca taatagctgc tttacctagt catgggtaat atgaggactg    19260
aatggcatct tttgcatgag tggaatttgt aaactgttaa gaaccatgca ttgttcttac    19320
actggcattt tctattttgt taaacttaaa attctttttt taaagtaaca aataaaaatt    19380
gtatgtttat gatgtacaac atgaagtttt caaatgtgta agttgtggaa tggctcaatc    19440
aaactaacgt gattacctca cgtactttt tttttttttt tttttttttt tttgagatgg    19500
agttttgctc tgtcacccag gctggagtgc agtggcacga tctcggctca ctgcaacctc    19560
cgcctcctgg gttcaagcga ttcacttgct tcagcctccc gagtagctgg gattacaggc    19620
gcgtgccatc acgcccagct aattttttgta tttttagtag agacagggtt tcaccatgtt    19680
ggtcaggctg gtcttgaact ctgatctcct gatccgcctg ccttggcctc ccaaagtgct    19740
gggataacag gcgtgaacca ccacacctgg cctcatgtac cttttttaat ggtgagaaca    19800
cttaaaatct actttcttag caatcttgac gtatgcaaca cattttttatt tactatgtca    19860 ccatgatctc ttgaacttat tgcttccgtc taactggaat tttctatcct tttgaccatc    19920
tcccagtctt ccttcttccc cttactctca atcccactaa aaaattctaa ttactttca    19980 ttctgtacct tctggggact tttgagataa tctttttagg tcagggccat gggatctttt    20040
tatttttagt ttcttcatct ctgatgctgt attccgttct ttttaccctg taccatttt    20100 tctcacaact tccacaaaat tagtttattc ttttatcctc cacctagtca cattactata    20160
cttctggaca gctggtccag tttgctgatt tttagacttc ttttttacctc attaattact    20220 tcatcaaata aggaagcatt tctgaatctg tacagcttta acagttagaa atagttgaat    20280
```

-continued

```
aacaagaagc taaaatatcc aatattagat tatagtcatt tgatgaacta ttataacatt    20340
aaaaatatgt ttagaaagaa ttgttaataa tgtagaaagt gctatcagtg aggaggatac    20400
agttatttta cattatacag aatctcaggt atgtattaca gtgtgtagaa catagggcta    20460
gaaggaaata ctccaaaatt taaacaaaaa gtaaccacaa acaagtggtt tcagtctctt    20520
tgtcttctta ttcagtctgt gtcttagtta cctggttttg tcccaggtgt ttacagaatg    20580
tggactctag ggagagttag aaagagaggg atgcagctga agcaaaaaca gctagcagag    20640
atgcaaggca tgatgtgata gatacaaaaa gggggtgcag acacatcccg tggttgttga    20700
gtgaagaggg agctccttct ggccaggaaa gtgggaattt ccagatctcc taggaatgca    20760
gtagaagttc atattcagtt cacaccttgg ataaaagcca ggcttagatt cttatagact    20820
caaacagaaa attcctgtgg tgcatttgaa gcagtataga atcctgggaa tcctggactg    20880
aaaatacaaa gacttcagtt aaatctttgc tctatcactg attttatctg tggccttgag    20940
caagttttga tgctttgatc ttgcattgcc ttttatgtca ctcgtagatg gtatataatg    21000
ccttctgtgc cagcctcaga atgctgttgt cagagtcagt cgagatacat tgattgtgaa    21060
tgcatcagaa ggtctattag tctatttaga tgccatgtat ttatgattat tatgatcgac    21120
aggatttgta ttccctattt gttctatgta ctgcctgaca gagtggactc tggcatctgt    21180 gattttttcaa acttttttt cttttgttg agacagggtc tcactgtgtt gcccaggctg    21240
gtctcaccct cctgtgctca agcagtcctc ccacctcggc ctcccacagt gctgggatta    21300
gaggtgtgag ccactgtgcc tggccagcat ccacaatttt gagggcattt gtaggtccag    21360
aaaatgttag aatctgtgtt ggatgagagg ctggacatag atccaagaaa aacaaaacta    21420
aaaacaggct gcccattagt cttgggggaa ggaagagaaa tgttgaacat ctagaaacct    21480
taggaaggtc aagaattctg gaacacgtat atcatttgac ctagtagttc tgcttctggg    21540
agtttatcct gtaggtgtac ttgtagttta tcctgtaggt gtgcagtatg gtgtgtgtta    21600
caaggttatt tcagcatgat ttgtaatagc aaatattaga agcaacctat atatccatca    21660
ttaaggggca ggttaaataa attttggcac atccataaaa tggaatactc tgcagctata    21720
aaaatgaatg aggatgcact gatctttaag ataatactcc taagtggaaa aacaaggtct    21780
actacagtgc tagagtgtgc tacttttgt gcaaaaaaag ggagacaaat aagaatatag    21840
ctttactgtt gcacgtgtat gcataaggaa actcagggg gtagcatgag ggttgggggg    21900
atacgtttga gagagggaag cttcactgct ttactgtgtg tgttatgtgt ttgtattttt    21960
aaaattttga accatgtaaa tatagtactt attcacaaac ttaaatttaa agttttttt    22020 aaaattttt aaacgaaaga aactctttgc aattggaagg caagtgaggt ggaagacaca    22080
ttgaatggtt gctatatgcc aggtcatatc catggaaatt tatttgaata agagaaccat    22140
ttgtttcttt taggtttatg gtcaaggttt aaaagaaat gttttaagct caccaggaag    22200
atgcccatta ttggtcgtaa ggtaagtaga atctgtgtat gtcattttt cccctcttga    22260 taatcatacc tctttctttc tatttactaa acctaatatt ctcaaagtgg agggtgatt    22320 ttgtctctta cctccagggg acacttggca gcatttggag acatttttgg tggtcacagc    22380
ttggatggag gggtgctctt ggcatgtaat ggatcgtgtc cagaaatgct gctaaacact    22440
aaacatccta cagtgtacag ggcagccccc ccccacccac caaacacaga attatctggc    22500
tggaaatgtc aaaatggcca aggttgagaa ccctgactta acccctttctc caatgtaact    22560 ggccaaagga gagatgagaa gcctgttaag gaagtaagaa tttgagaaaa cctgactgta    22620
ttgttaggtg ctttggaaca acatgcagct ggctgacttt aggtatttat ctaggagttg    22680
```

```
ggtgcttaca tggtttaggt cagggggtcgg caaatgtttt ctataaaggg ctagatatga    22740
aacattttgg gctctgtagg ccatatcatt tctgttgcaa ctcctcacct ctgcccttgc    22800
agagggacag cagcaagagg ttcaggaatg agcctggcta tattccagtg aaactttctt    22860
tacgaattca ggtaggcctt tgttggttcc tggctgtagt ttgctgatcc caagttgcac    22920
agcgctgtct cttgctgttt gcaattttct gtattgtagt atgtcccctt tgttatgtcc    22980
tcttggccct catccatgtt gaggataagg tagtcacctc tgtgcgtctc ccacaggtta    23040
tcccagatga agataaacag ggcaggccac ttggcaagct ctaaggaagg catatgagtc    23100
cttggaatct tcatctcctc cagtgccctc ccctgacccc cctttggtct ttcccaactt    23160
tacctgcctt taagttttct tctacttttg gctttcagtt ccctttcctg gctataccag    23220
ggtttgtttg ccaaccccctg acctaaagtt ggccagttat ctttaacctt tggctgaaat    23280
ccattcagat cgctgtgcta actctcccag agataggtat cttcaggttc atttcctgta    23340
ggagagtggg agcaataaca ggtggtgaag ggaaatgtga gcatataggc ttctgtttgc    23400
tctccaaatt atattaatcc ctaaaagtaa atcagtcct tacagagtat aaggggtggg    23460
gacagggaag gtattgtaga agatggactg tagcacaaag gagattagga tttcccctta    23520
tctcctgaat tttttttttct tcttttcgtt cagttttcag actttgagac aaataaatgc    23580
tagggttcca gaacccactc ttaaacttag aaagtaacag aattggaaga tccttagctt    23640
gccaaggact atccaatcac tctccatttt tcagaaacag attctgaggc ttagatacaa    23700
aaaattacat gtgtgtatgt gtgtgtgtgt gtgtgtgtgc gcgcgcacgc gtgtgtgtat    23760
acctctgtca tttattcact taacacatgc ttattgagcc acctgctcag tgtcaagtac    23820
ttttctgggt gctggggata tggtggtgaa caagaccaaa tccttcctct catggaactt    23880
acattttaat aggaaagaca gaaaataaag aagtaaacaa atatgtggaa ttttattttg    23940
aaataaatgc tttgaagaaa ttaaaattgg gtaacgtaat acaggctttg aggcaagaat    24000
tgggggtaag gaagtacttg tgcttttctaa tatacctctc tgtcactttt tgtctgtttt    24060
atggcaatag catactctat gtatggaagc tcagctttca tagcctgttc tgttgcatga    24120
gtcgccattt atgtgaatta attttttaat ttacaactta aaaaatgtct tcacatccat    24180
agcatgccca ggcattgccc aggagtgtag cctctgctcc ctgccagtgt gggcctctta    24240
gactattgca gacatgctcg aaaggagtgg cttttcctgt ggtttcactg agggccatat    24300
ctaagaagat cttcttgtat tctaattatc cttggctaga gatgagaaaa tcttagtgtg    24360
gagtgagttc tggcgttctt taacaaatat attgctgaaa caatagcact gtgacaaatc    24420
gtgacatgta gcttctctcc ccaaacctac tacccaagag ccttttgcta taagcagcag    24480
cccctgccct tctgcctcct tactctgcta ttttttttcc ctcagcactt tttgttacct    24540
gtcttactat tttctgtctc tcctgctgaa aataaacttc atgaggacag gaggtttttt    24600
ttcctgtgtg ctccattgcc taagtttgtt ttgttcacta tgtgtccctg gcctgcatat    24660
ttgtgaatat gcagtgaata tgaatgtgaa tatgtaagtg aataaaagaa aacagctcag    24720
aagctgtggc tttgaggatg gaaagaagg gaaccatagt tgataaacta cctagcagaa    24780
aggaccttag ttccttttaa tattttgggg tcagacagtg caagctgtcg acagcagctt    24840
aaggagatac attagagtct tcctggcagt tcttagaatg ccttgtgcta gtgttgaatg    24900
ggacctccaa attcctagtg tgctgcgtgt atgtctgttg aaggagctca tcacttgcac    24960
aaggaccaga atcacttta ctgcagcatg gccagttttc tggccactgt tcctagttat    25020
```

-continued

```
acctttgatt cttttacaca cacactgtag ctgctgccaa ggcaggatca aagtccaaat    25080
actgccctca aggatgtgct gactttagca atgccaacca agtgaagcag cagtgatgtc    25140
aatgtggcag agaaaagggt tatggggaaa ttgggtgcaa cttttttttt ttttttttg     25200 agacagagtc ttgctctgtt gcccaggctg aatggagtac agtggtgtga tcttggctca    25260
ctgcaacctc cacctcctgg gttcaagtga ttctcatgcc tcagcctccc aagtagctgg    25320
gattacaaat gcctgctacc atgcctggct aattttttgta tttttagtag atgggggtt    25380 tcaccatgtt ggccaggctg gtctcgaact cctgacctgt aatgatctgc ccacctcggc    25440
ttcctgaaga gctgtgataa taggtgtaag ccaccgcgac cggctgagtg catcttgacc    25500
tttagagaga agcttcgctt ttcaaatttt taagaggcta ttgtacatgc cagaaagtag    25560
ctgatcagtc agaatatcac catatatctt taggaaaaat gttagtttag ttacttgtgc    25620
ggtgcctagc attgagcagt tgcttgactg tcataataat tctgctgtct ctactgtact    25680
cttgcatctg gataactttg tctttcttac ctttggagat tcaagacaag ttgaacaaga    25740
ccaaggatga tattagcaag aacatgtcat tcctgaaagt ggacaaagag tatgtgaaag    25800 cttttaccctc ccagggtctg agctcatctg ctgttttgga gaaacttaag gagtacagct    25860
ctatgggtat gatgcttggc atatacatgc tctctacttc cttaaagaga caggttttgt    25920
cattgtttaa tgttcacata ggttaagaat aactcatcat tggttaatac atgtttagga    25980
gggcctactc tctgtttcac aggttgaatt tcctattttt aaaattatgt ttagattcat    26040
ccttcatcca taaagcaagc aaatctcaga gacagtggaa cttggctttt atttcctttt    26100
gtaagcatga ataaaacaaa tatatttgtg tttaagaaga gagaatataa gatatgtaat    26160
acaaatgaaa tacagatcca tgtaaaaatg tgaaatctgc ataaaggcac aaaagaaaat    26220
aagtcactat aattccacta tcaaagataa acagatggtg tctatcttta tgcatgtagc    26280
tataggtaga gctgtctata tagtttacat ctatctatat atgtatatct gtctgtttct    26340
gagaatgcta atagtgtttg tctgtgtgta tacacatgta tgcatgagca catatgggat    26400
ggataaatag accaaatagc ttggtgctta agagcgtaac cctggaacca gcctggattc    26460
ataccttggt ttgccactta agtatgcct ttggcgagtt acttctgtat gtcacagttc      26520
ctgtatctct acaatgggga tagtaatagt agtacagtac ttacctgaaa agatgattat    26580
ggggattaaa tgagatcata catgtataaa tgttttatag tgcctggcat atagtaagga    26640
ttcagtaaat gttaaacatt attgctatta ttaactcaaa cagatttatg tttgttactg    26700
attaagatca tattacaagt acttttttaaa aagaagcttt ttagtttgat atatttacag   26760
aaaagtagca aagatgatag agatttccct atacccagct tctcctgatg ttaacatcct    26820
ctataaccat ggtacgttta tcaaaactaa aaaattaaca ttggtacagt gctattaact    26880
acactacaaa ttctatttct agttcatcag ggtttttttt tgttttgcta tgttttgttt    26940
taaactaatg ttcttttttc tattctagga gccaaccagg agccatgttg cattttgaca    27000
aatacccttt ttttttattt tttgagacag agtctcactg tgttcccag gctggaatgc     27060 agtggtgtga tctcagctca ctgcaacttc caccttccag gcttaagcaa ttctcgtgcc    27120
tcagcctccc aagtagctga gattacaggc gtgcggcacc ataccagct aattttttgt     27180 gttttagta gagataagat ttcaccatgt tgcccaggtt ggtctcgaac tcctgaactc     27240
aggtgatctg cccaccttgg cctcccaaag tgctaggatt acaggtgtga gccactgtgc    27300
tcggccttga caaatacct tacaatttct aagtgacatg tgttgaggtc ttgacattga      27360
atagtacaaa atttgatata gtctaggatg tagatgaata aagcagtggt tagcactcta    27420
```

```
aaacctggtg ttaaagattt ccatgattat gagacctggt tgccgccatc atattgcctt    27480
ctctttaatg tttaagtcac tgtccattgc tgtattctct agcatcagta aaagaacagg    27540
aaatgaaacc agttatctta tttttgaaag gctggtgacc actggtctga agctgtgtat    27600
agtacagagc agtgtcctct aaggaaagag tgaaagtcaa acgggcagca agccagagct    27660
tggcagattg ctgtaagaat gagtttgtct gtatatttac cacttagttt tctgttctca    27720
agagctgaag atctttgctt tggagagccc ttggctccat gcagttttta gttggtgtgt    27780
ttccgtaata gctttctcac tacccacttt caatagggca cagctgcatt gtagcacaag    27840
gacctgagac acccatatca acaaatttgt gggtaaaatg aagaatgtct cggggagaga    27900
ggaaagtgga aagtcagatc ttatattcta ctcaggaact ttacttttct ttccacactg    27960
ggataaagga ggtttatccc aatgttgact gtgttcctga tcttgaatat gctacagcgt    28020
gtgctgctgg aagcaggtaa ctagttttat gtgggtttcc aggcttggct taagggagcc    28080
ggcgtctgag accggggtgc tcatggttta tacctcattg tggtttgttt gctggtttca    28140
tctctgatga tagtgtgctg aaatttcaca ctttttcattt tgctttcttc tgccaactct    28200
gctcataata gttctcaaaa ttcctaggac tggataggaa aggagagaag aaggaagcta    28260
ttgcagaaaa aggccactcc aaagccatat agagaacaaa aaataagtat agacaaaggc    28320
aaatgttcct gctgttagaa ggcagttgag gatgaggaca acattattat cagattgcct    28380
ttattgtagc taaatgctat taatatcttt ttcacattgc tgataataat gattttcat     28440 ctttatttta ttgtgctaac tctattgaac ttttttcttg atttgctata agaatgctgt    28500
tgggtttcca ctcaacattt ttttcttttg tatccagagg agtttcttcc tgtttcttct    28560
ttatcagaac ctgtcttccc agagattctt gcttactgac cagtgacctt acctttctct    28620
gcagacgcct tctggcaaga ggggagagcc tctggaacag tgtacagtgg ggaggagaag    28680
ctcactgagc tccttgtgaa ggtgagtgtc cagttcttga gggaagcctg tgaggtctgt    28740
gccagtttac atgacctcct tttttttccct tactttgta attagaaaaa ttacttaagg    28800
aaagcttatt ggtacaataa aaccataaaa gtttctcttc acccaaacat aggcgaatat    28860
gtataatatt atcaaagaca tcttcagtct gtaaaatagt aaaatgttat ttatgttttc    28920
agtctttgca gatgtcctgt ctagaaggca gattactagg gaaggtagtc ctgtcagatg    28980
agatttttgt ggtgagacag atttttgtttg ataagaagag ataagatagg gaaactcttt    29040
cataattttc tcaaatcatg tgacccaaga tgagcagtgg tctcatgtat acttcaaata    29100
attctcattc ttagcttctt ccatttctaa tcaaatttat ttttatttta ttttattatt    29160
tttacagaca aagtctcact ctgtcacaca ggctggagtg gagtggtgta atcatggctc    29220
acttcagcct tgacctcttt ggctcaagtg atcctcccac ctcagcctcc tgagtagttg    29280
ggactacagg cgtgcatcat gacacccagc taattttttgt atttttttgt tggagatggg    29340
gtctcactct gttgcccagg ttggtcttca actcccagcc tcaagtgatc ctcctgcctt    29400
ggcctctgaa agtgttgaga ttacagctgt gaaccactgc actcggccct catatttatt    29460
tttgaaactc cacttcatca tataaaattg gggttgtact gatgatctct aaggtctttg    29520
tgtttgatta ttataaatat gaaactgtcc cttactaaat aaatatggca ggttttgcat    29580
aagttggtgt aatgctctga tcttctgtgc ttaaaatctt tcagtaggtc ttcaccacgg    29640
ggcggaagga ccgcgtgcac gcccagcata gtaccaacgc gaccttccac cccgggtgaa    29700
gactcatgct tttacgttgt tttccttccc ttccatcatt cctcttgttc caaatgatga    29760
```

-continued

| | | | | | |
|---|---|---|---|---|---|
| ttcctactca | tctctcaaag | ttccactcag | cagacacctc | tagatcactc | aggatgttag | 29820 |
| ttgttccctc | ttcagggtcc | cttagcactc | tgtacacaca | cctgatattg | cagtcgataa | 29880 |
| caacagctgc | tttgtgccag | acactctact | aagtgcttca | catgcattat | gttatttaat | 29940 |
| tattgctaga | acactagaag | atagctacca | taacaacttc | tgcgtatgaa | gaaacaacct | 30000 |
| tagattatgt | gacctacaca | gctgaaagta | ataggcaaag | cttagacttc | ctcctgggtc | 30060 |
| ggtttggtgt | tatagtctgc | gcttttaacc | atatttatac | ttctttcctc | atcacattgt | 30120 |
| aaaattattt | atttacatgt | ctgtctcctc | tgctatgttt | tgatcttttg | gttgaggaat | 30180 |
| atatcttatc | ttttttttcca | gtttatattg | ttgtgcctaa | tacttagaaa | ctgttgttta | 30240 |
| gtgcatgatt | ctttgtcctg | tatagtgtaa | tagttttgat | ttcacatctg | cttgcattttt | 30300 |
| tttgcaggct | tatggagatt | ttgcatggag | taaccccctg | catccagata | tcttcccagg | 30360 |
| actacgcaag | atagaggcag | aaatcgtgag | gatagcttgt | tccctgttca | atggggggacc | 30420 |
| agattcgtgt | ggatgtgtaa | gtatatgcaa | ggggcatcca | atagccttat | ttttttaggtt | 30480 |
| aaaatagaag | agttttttaat | aaatattaat | tatattttaa | aaataaaaaa | atattaaaaa | 30540 |
| tattttacta | cacaagaaat | atttgatcat | tgtagaaagg | tcattttact | acacaaggaa | 30600 |
| tatttgatca | ttgtagaaag | atcctaatta | actgcagttt | taaatgttac | ttgtaatttt | 30660 |
| gtaacctaga | caatgtcaac | attttggtat | atattcttct | agatattttt | attttcacct | 30720 |
| ttttattttg | aaaactttg | aacctacatt | gagttgctag | gatggcttaa | agaacaccctt | 30780 |
| agattcacta | aatgtaaata | tgttgccata | tctgctctct | acactctttc | cctccctacc | 30840 |
| cgcttcttcc | ctcatcccccc | acctgcatac | ctaccattcc | cctatttatc | tgtgtatact | 30900 |
| tttgttgttc | catccagcag | tgttttttagt | gtacttctgg | ttttacctga | gccaaagttt | 30960 |
| aatttattat | tttgctgtaa | actgaacctc | atttagttgc | tattaggcat | aaagaaaggg | 31020 |
| ggaggacatc | attatatttta | aagaaacaca | tgaggattct | ttgttttacc | tgttctttca | 31080 |
| agtagatggt | tgttagtttt | cgtaaactat | gatagataaa | cttctgttta | gatctgttgt | 31140 |
| ctttagaaaa | aacgaaatct | caggttatgt | aggatagata | gatttaactc | aatatgctgc | 31200 |
| aatggtgtcc | tagaggtgct | aatcctatca | gatactcatc | atatttgcag | tcattataaa | 31260 |
| gactgcagat | ttaattattg | aagggcccat | tcgaagagca | cctaatttag | tttcttttttt | 31320 |
| tttttccagg | aagcattgtt | tttgtttttgt | ttttctaata | tgttggcgcc | atgaaaatca | 31380 |
| tcatgttcaa | atattagtag | taataaaggt | gatatgcctg | gcattcattt | tcaaagcaaa | 31440 |
| atactgaaac | tgttaaaaac | agaaccaccc | ataatacagc | agcagtttcc | cttagagtac | 31500 |
| tgaggtgaac | agggtgactt | tcagagggaa | gatgataatg | tacttacagt | atattctcct | 31560 |
| atgccattag | actcttgaag | aacttgtaag | aggccagagt | gaatagccac | agaacagttt | 31620 |
| ggccttatct | ggtaaattttg | aagatacata | tatcttatga | cccagaaatt | ctgctactag | 31680 |
| gacatactct | agaaaaatta | gtacacatat | atatcaggat | atatggacat | taatattcat | 31740 |
| agcaatgtta | ttcatgatag | ctaaaaactg | gaagtaattc | aaatgcctat | ccacaggaca | 31800 |
| cagatgaata | aattgtggaa | tgctgtgtgt | gcctcaatcc | attgtagctc | ttattcagat | 31860 |
| tgatgtacaa | attgcctcat | ccatctttgg | ccagtggaaa | catcatattg | gctcctaggt | 31920 |
| ccatttacat | gacccaagta | atctttgaaa | gcctttttttc | tctttctttc | ctttttttttt | 31980 |
| tttttttgac | gaaatattcc | aggttcaggt | tcactttgtc | catttcctgc | tccaggcctt | 32040 |
| caatcagcca | tttatccaag | gagccctggt | tcatttaaaa | ctaggtaaaa | taattacata | 32100 |
| gttccaaaat | cacatttatg | gaacaagaca | gattaaaaaa | aaaaagttaa | ccagaatgca | 32160 |

-continued

```
gtccagagag acaaagaaat agaaggtatg aaagagaggc taagagatgc aaaggatagg    32220
atgagaaggc taacacacat ctaactggtg tttgagagca gccagagaaa atagattacc    32280
tacaaaggca taactgttag gacaactgat actcaatagc aacgatggct ggggcagttg    32340
ggggtagatg aaagattggc tgtaaattga aaattgctgg agcctggtga taagtagtga    32400
gaggtcacag cgtgctggca gtcctcacag ccctcgctcg ctctcggcgc ctcctctgcc    32460
tgggctccca cttttggcgg acttgaggag ctcttcagcc caccgctgca ctgtaggagc    32520 cccttttctgg gctggccaag gtcggagccg gctccctcag cttgcaggga ggtgtggagg    32580
gagaggcgtg agccggaacc agggctgcgc gcagcgcttg cgggccagct agagttcccg    32640
gtgagcatgg gcttggcggg ccccgcactc ggagcagccg gccggccctg ccggccccgg    32700
gcaatgaggg gcttagcacc cagccagcag ctgcggaggg ggttctaggt cccccagtag    32760
tgccggccta ccggcactgc gctcgatttc tcgctgggcc ttagctgcct tcccctgggg    32820
cagggctcgg gacctgcagc ccgccatgcc tgagcctccc accccctccg tgggctcctg    32880
tgtggcccca gcctccttga cgagcgccac tccctgctcc acgcgcccca gtcccatcga    32940
ccacccaagg gctgaggagt gcaggcgcac agcgcaggac tggcaggcag ctccagtcct    33000
gcaggcagct ccacccgcag ccccggtgcg ggatccactg ggtgaagcca gctgggctcc    33060
tgagtctggt ggagccttgg agaaccttta tgtgtagctc agggattgta aatacaccaa    33120
tcggcactct gtatctagct caaggtttgt aaacacacca atcagcaccc tgtgtctagc    33180
tcagggtttc tgagtgcacc aatcgacact ctgtatctcg ctgctctggt ggggcttgg    33240 agaacctttg tgtggatact ctgtatctaa ctaatctgat ggggacgtgg agaacctttg    33300
tgtctagctc agggattgta aacgcaccaa tcagcgccct gacaaaacag accacttggc    33360
tctaccaatc agcaggatgt gggtggggcc agataagaga ataaaagcag gctgccagag    33420
caagcagtgg caacacgctc gggtccctt ccacactgtg gaagctttgt tctttcgctc    33480
tttgcaataa atcttgctac tgctcactct ttgggtccac gctgctttta tgagctgtga    33540
cactcaccac gaaggtctgc agcttcactc ctgaagccca gtgagaccac gagcccaccg    33600
ggaggaacga acaactccgg acgcgctgcc ttaagagctg taacactcac tgtgaaggtc    33660
tgcagcttca ctcctgagcc agcgagacca cgaacgcacc agaaggaaga aattccggac    33720
acatccgaac atcagaagga acaaactcca gacgtgctac cttaagagct gtaacactca    33780
ccgcgagggt ccgcggcttc attcttgaag tcagtgagac caagaaccca ccaattccgg    33840
acacagtaga agcccattgg gcttttcaat tttatttact ctaatttcat tctaaagaat    33900
tctgttttgt agttctcctt ttatttatt attattttt gagacagggt gtcactctgt    33960
tgctcaggcc agagtgtagt ggtgccatct cagctcactg cagccttgac ctctctgggc    34020
tcaagcgacc ctcccacctc agcccccttg agtagctggg actacaggca tgcaccacca    34080
tgcctcgcta ttttgtat tttagtaga gatgggttt caccatgttg cccaggctgg    34140
tgttgaactc ccaagctgaa gtgatctgcc tgccttggct tctcaaagtg ctgggattac    34200
aggcgtaagc caccacgctt ggccgtcttt tttttttt tttttta atctgcttgg    34260 ttgttttta tagtccttt ccttggctta acttttgttt acttaaatat attacacata    34320
aatatgttgt attctgtgtc tgataattcc aatatccatg agccttacct gattctgctg    34380
gcttcagtca tggttccttg tttccttata tttgtgattt tatttttt atttatttt    34440 ttatgagcca ctcattttc tgggaaccta gggattcttt gaggcctaga ttgaagttaa    34500
```

```
gtctggaagt tctcttcttc cagagaagat ttgtcatacc ttttgagtt gctgggatt    34560
gccaccacac tggaaccaaa ttaagtcaaa tccttagctt gtcattttgt accacagagg    34620
tagtgtgaat tctgaccaca aactcacata aaggcttcct tgttacacat tcttgaaaga    34680
ttgctatttt tctttacttg aacatcaggg ttgagaaaaa cagtttttct tttctctttt    34740
gcagtagtgg gatttatttc ttgtacactg tagagtgtgg tcttttttcca gccatctcct    34800
gttggactcc ttatcttggg cagtctctaa tgtatcttct ggtccatcct ttgctcatct    34860
gtcagtgtag gagtttgaag tctgaagggt ctggtgccac ctcagggtga aagctagttt    34920
tgccactcac ttatcttgca ggattcttga ttttgctttg tttggggggtt tagcaagttt    34980
ctttatgtta ggttagtgat aggtttaaat tttttttttt tgatgtttta tcaagttttt    35040
tagttatttc agttaggaag gttgctcaag gtatataata ttgctagaaa tagaagttcc    35100
ataattgttt tttccatgtt acagaccttc gtctatttga agcccctttt ctccctgaat    35160
cttctctgcc ccacattttt ctgggttact ccgcttttca tatgatttca cagacttcca    35220
accatcgcag tcattctctg tatgactttt ggttgcctct ggccagattg aacacagttc    35280
tccacatttg gagtggcatt gatctttcaa tctctgtctt ttttaaatct gggttcaata    35340
aacttatttc agacctttc cttgaagtca gcattttat tcttggcaat gtttatttta    35400
ttccttgctg ttcctaatgt ctttgttagt tctgtatgga tgctactggc tttgttttt    35460
taggtctgta gctcattctt tttgtttcat ggtctaggtt ttgaactctt tgttttctta    35520
aattcatgtt cttatgatat tttcctatag tgagaaagtt ataagggggtt tccttcatcc    35580
cttagctgtt tccttctgtg ttgggttttt attttgcatg ctacatacta cctttttcccc    35640
tgccttttag tttgtttgca tagtttcctt gccatttct ctcatcttgg ggtggcattc    35700
tccagacatt gttcttatgc actgtgggtg cttcctgtct gagaccattt ggctggggac    35760
aaagctcagc caaagctttg ttctatctgt attagaataa ccaggtctat tctgagattc    35820
tcttcaaagt tacctatcag agttcactct cttatttgga agagataata tacccttga    35880
gctctgatta tttaattcac tgaagtcttc actctaaaga gccaatcctg atgttctctc    35940
ttcattttgc tcatttctcc ctagcagcca tgtttaccac tcactcatga gaagaagaag    36000
aaataagga aaccccctca gcttgcctct gcagatttgg gggtataaag gaaaattctc    36060
aggattttgc tgactttgcg gtacagtttc aagggctgat tagaaactag tgttttgctt    36120
acttctgctc tctgctgttt cactgttct ttttttttttt tgattgccaa tatttgaagt    36180
ttattgccta gattatctct cttttccttgt ttggttgttg ttattgtaga ttttgactct    36240
tttctctccc tgcactcacc cttttttttt ttcttcccat cttactcctg aagtccaggc    36300
ctagggggttt tttgcattgc tgcaattaac ccatatctct attattttga tctccagcac    36360
gtgtgaggga tcagaagaag gatagagtct gattcccagg ctcttctaat atttagactt    36420
ttataaaata actaatcagc actggtattg tgctttttcc ctctcccact ctgtctcccc    36480
cactcctccc ttagcttctt acttctctct tggatgagc tgcttctagt gaagaaagag    36540
ttcactgttc agaggtggga agccagaaga taaaaccaaa tggctgggca gtctttaggt    36600
tattcctagc taagagttaa gagttgtaag ctctctcatt ctttgttctt cagccttaaa    36660
ctatctttcc ttctattaac tttatttgtc tcagttacaa tgatagaggt aacttcacat    36720
actaaaagaa attaggttac catgtgaaac attcttcttg gcttgtgcta atgttatcag    36780
atccaaacag catctgaaag aaaatttcc aagtagatgt tgttctcttg ttttctgaaa    36840
tacatatcat atgttaaagt gagagttttt atacatgttg aaagaagttg aatgacataa    36900
```

```
caaatagtta ctgaggcctc cattttctta cttcacagtt aaaattcctg tttctctttg    36960
ggtataggag gtagaaagaa gtgggagagt aatagcattt taaaacacag aatcaaaaat    37020
acatattaaa agtagaactt aggcccaggc acagtgactc acgcctgtag tcccagcacc    37080
atgggaggct gaggcaagtg gatcgctcga gcccaggaat tcgagaccag cctgggcaac    37140
taggtgaaac cctgtctcta caaaaaatac aaaagttagc caggcatggt ggggtgtgcc    37200
tgtagtccca gctactttgg gggatgaggt gggaggatct cttaggcctg ggaggtggag    37260
attgcagtga gccgagatca cgccatggca ctccagtcta ggtgaaagat tgagacccca    37320
tctcaaaaaa aaacaaaaaa gaaaaaagta gaatttaggt attcctactt ttacagtcaa    37380
aagtccactg gtgtttgcat aacaatgatg ttttgactag ttattggact aaaagtagga    37440
cacatgaagc aggtgactag gaatttggaa atattattgc ttaggtcatt actggacctt    37500
acgaagagat tgttgcactg gtgacttgga ctttgctggt ccctccccga ctcttcacag    37560
ctggcttgac gactcttgtg acattctgag gttttatgct aaaccacagg acatgctgct    37620
gatttgcaga gctgacctca gctgtaagca cttttgtcttc tgcagcgtag aaatgtagtg    37680
acctacaagt gtcccatgcc caagttgggt gcattatttt ttggtgatgg tcacatgttt    37740
cataaagact tcctgagtca aaaatgact tttctcagtt catcttccat ataactcctg    37800
gccacaggga ttttgtatcc aatggtattt ttgttctatg tgtggatatt attttagcaa    37860
agttcagtgg tcactttctc tgattccatc ttgtattaag ctacactaaa tatgaaaacg    37920
tagaaagttt tacttcttat caacagatgc taatgtatga cattgagtga aacactttaa    37980
ttcctcaagg gctcagtttt ctcacctgta aattgaaaaa accttcaaa gattgtatga    38040 atcttcagag atggtaagtc taagaagttg tccaactagt ttagtattgt ggcttttttgt    38100 ttgttttgga atgattcatt ctcatatatt attttttaaa aaaatagcca ggtggctatg    38160
acatgcctgt gttggtcaag gtttactgag agtcaagtca ggcattaaga aatgtgaagg    38220
ccaggtgcag tggctcacac ctgtaatccc agctctttgg gaggctgagg tgggcagatc    38280
acttgaggcc aggagcttga gaccagcctg gccaacatgg tgaaacccccg tctctgctaa    38340 aaatacaaaa attaggtggg catggtggtg ggcgcctgta atccgagcta ctcgggtaac    38400
tatggcagga gaatcgcttg aaccaggagg caaaggctgc agtgagccga gatcatgcca    38460 tgcactcca gcctgggcaa cagagtgaga ctctgtctca aaaaaaaaaa aaaatggat     38520 tgagggtttg ttaggtgtca gccactatgt caggtgctag gaatttgtca tgaacagact    38580
ggtccctact ttcatgaatt tatagtccag tgagggaaat aagatgaata aaaagacccc    38640
tacgtctttt tgtttgaact ctggtaaaga aatgtgttta tcagaggggc taggccaaac    38700
tttaggaaaa catttcactt cacttaaaaa aaattaggat ttttgttttta tttcagataa    38760 ggcaacaaac ttccatcaag tagaaacttc tgcttttctc tgtctttcaa acttgtcaaa    38820
atcagcagtt tactttgtta aatctgaatg tctctttta gtgtattgca cagtttacta    38880
gaattgtaat cacaatttca cattctttaa caggtattga aaatttaaat taaaattctg    38940 atattttga atggcataaa atgccctatc ttatctgaaa attgaaaaat taatacagaa    39000
atgtaaatgg attgtgaata ggtgggatct ggccaagtgt gcatttgtct aggcagtgct    39060
gagtttctgc tcattattta gtagctttca ttcttcacct gagccaaaat taggcttagc    39120
caataaagcc aaatttttcct tctggaagac atggcagtgt ctgccttgca gcatgcatcc    39180
aagaccttat ctgtttctgt atcaaacatt gtcaagatca gggcatgaag agccggggca    39240
```

```
ttcctgactc ccccaacaga tggcatctct tctttattat aggtgacttc tgggggaaca    39300
gaaagcatac tgatggcctg caaagcatat cgggatctgg cctttgagaa ggggatcaaa    39360
actccagaaa tgtatgtatg tgtggctgtt ttgtcccctt ttggatttgt ctgtctggag    39420
tacagcttta tgaaactaaa gcagataatc cattttcctg ctgcttctct tcctctggta    39480
attctggtcc cctttccccc tgtcctagcc cctctgccct tatccttta cattcagtaa     39540 aattctaaat ggatcagcca gttatttta aagatcattc ccatcccgcc ccaccccag      39600 atcatgcata gtatatacta caagcaaaaa taagatcctt tttccaaaag tgagagtttg    39660
aggactacat ctttgaatcc tgtgatattt gcaaattatt tggagcctaa agaaacctct    39720
ctaggtactt tagttctgct taccttagaa agttacttaa tattataggc tgcctcaggg    39780
tactctctgg gaaaacttta gtgtgagggc tgttttctgg gaggaagaat aaaaatatct    39840
ttttgagatt tacccacatt gccttccttg gacataaatt tgatgtttag ttacattatt    39900
ttttcctaga ctgtccccctt gtacagtatg tttatcctac atcttaatat ttttactgca   39960
agtattactt gacaatgggg atttattgca tatggtctca tgctgtggtt catatgtagc    40020
ataagagaat aaaccaggct gccattcttt cttcatatgt cgatctttgg tgcttggtac    40080
ttcctcagta gtagagattt ttctccttag agggaacaga ttcgttgtat gaatggagta    40140
gttgaggaaa gtctaaagca aatacccgtg acctcatttt ctctttcaac actatttgaa    40200
atactatttc caaatgtgta ggagaaatgg ggattttagt ttcttcaggt ttgttgtctt    40260
tcagagttgg aaggggccac tgagctgatg cttggccgct gtgtgaacat ttctgcttga    40320
acatgtgttg tgccgggaag ccttcttctc attctcactg aggtgcctgt ctttggtagg    40380
caaccgttag ccagctctgc cttgtgttgc tctcatccaa agtctctgtc ccccagcttt    40440
ccgcctgcca gcctagcttt atgctttgga tccctcactg tgggatcact tctgagtcct    40500
cttcctattg ccagaatgat ttcctaaata ggagggaagt ttctgcagaa aatcagttgg    40560 cctcttttg ggtgtgctta aaagaaaag tagagcagtc taaacactta aatttttaat      40620
ttggggaaaa ataatcagaa cttactcccg gtaatttaga ttagctgcta atggtgtttt    40680
ctattatttt ggcctgagtt acattattct cctcttccct gtcatttagt gtggctcccc    40740
aaagtgccca tgctgcattt aacaaagcag ccagttactt tgggatgaag attgtgcggg    40800
tcccattgac gaagatgatg gaggtggatg tgcgggtgag tccctctgga gggcccactg    40860
tctgtgctgg gccctgacag cagaagggcc tcctgttga ctagccgttt ccagtcagat     40920
gggtctgact gcctttgatt gtggcagcca gaatatgaaa aactgcattg atagtggtga    40980
ttgactgcag cttcagtctt ttcataggtt catgaattct gaaagggagg tgatctagtc    41040
actaacttgg gacttgagag acactggttt tgcggtcagc gccatcactt tttctttctt    41100
ttctctattt gtaaaatgaa catggactca cttcccctaa gactcttacc atggcccggg    41160
catggtggct cacatctgta atcccagcac tttgggaagc cgaggaggga ggattacttg    41220 aaccctgag cccaggagtt tgcgaccagt ctgagcaaca tagtgagacc ccatctctac     41280
acaaaattta aaaagtagc tggacatggt ggcatgcacc tgtagtccta gctactcggg     41340
aggctggggt gggaggatca cttgagcccc aggaggttga tgctgcagtg agctgtgttc    41400
acaccactgt actccagctt gggtgacaga gcaagaccct gtctcaaaaa aaaaaaaag    41460 actctcactg tggtttagat tggcttaaat taataccatt gtcattatga tagtgattat    41520
ttttatgcct cacatttgtg tagaggagtt ttctagtttc agtgttctgt cagaatccca    41580
tttgagcttt atgacattcc agagaggttg atgaagctgt tatattattg tagttcacag    41640
```

```
ataaggaaca gactgaagta gcatactcag ggtttcactg ctggtacgtt gtggggctgg   41700
ggctcacatt tggctctttg gcctcttagc tcaatattat tttcgccccc acagcgattc   41760
tgttcttatt ttgtgctctc agactattct ccaaatggac ttacctggag tcacctgtgt   41820
cctgtcaccg tggtgggatg cagtcttctc ccagttggag tggtgaagga gggggtactg   41880
gtggaactgg aactctaagc tagcagccca aattgctctt ggcagcagaa gagaagagta   41940
attgtgacat agattctcat tttccttta actttaaatc cctaggcaat gagaagagct   42000
atctccagga acactgccat gctcgtctgt tctaccccac agtttcctca tggtgtaata   42060
gatcctgtcc ctgaagtggc caaggtatat gagagaaatg ggctgctaag gcaggcaaat   42120
ggatatttta aaacaaagcc taatggggca gtacttggca aatagaagcg attttttttt   42180
tgtttttgac cacagtagtg ataagtagct ctcatcagcc ctaggggaag ccctgcagct   42240
cagttgcaag cctttaaaag ttgctagtct ctgctgtggg ggaagatagt acaaggctga   42300
ggccttttaa actggaaatt ctgaaatagg attgccttct agattgagat ctggaaataa   42360
tctgcatgta ggaatgtgcc caccaaaagg gtgatattcc acatgctgcc cctcagcgcc   42420
tcccttttcc tcacgcctca tcctgcagtg actgaggcag gacctttccc ttgtgcgaga   42480
ggcagcctaa atcagagctc tactcatttc ctgcttgata ccgcagagcg tttgaggtca   42540
tgcatattta aatataaaat tgataccata tttcagatga attattttga agggaaaata   42600
catttgaaag ataaattttg ttgggaatgt taaaaatagc cattttttaa aaacatggga   42660
ggcataatac aaaatagcct tgtgtttata gcccatcttt ccacccatgt cttgcagttt   42720
ttattatagg gctataaagg aaattctctt atgttctttg ttttttggaa caagctggct   42780
gtcaaataca aaataccct tcatgtcgac gcttgtctgg gaggcttcct catcgtcttt   42840
atggagaaag caggataccc actggagcac ccatttgatt tccgggtgaa aggtgtaacc   42900
agcatttcag ctgacaccca taggtgagc taaggaggag atcaagtgtt accagttgat   42960
tattttgact attattgata aaataaattg gtagcttccc cgcaaagtat aaaattaact   43020
atagaattct catcagatgc ttgttttaaa ctctctcttt gccgtcacca gatcagctgg   43080
ttcaggtgat ggggtatagt ggtagaggtg acaagcagta gtgaaaatga acctgttacc   43140
tttatctcaa attggctaag agaatttctg tatccactga ctgtgtgtaa ctagaacatg   43200
ctagtgtagt ggcccttgtt aaaaaagctc cctgaagcct tgagctgatt tgaggtggag   43260
ggtagaggag tgtgagggtt ggtagtggag ttcccatgct ggtagataac attagagctg   43320
ctgtgcaact gggctcctga gcgtacatga cgggaaaatg ttgacggaag agtccttttgg  43380 aaaatgggaa gaacctgtgt gctcaggaac attcagcatt tgagatggcc acgcctgcca   43440
cccttggtgg actgagacaa agtctagatc agttgataac gctattgaat atacatccag   43500
atgtggaaga agtattagca gcctcaggaa tgtgtacctt gttttgattg cattttcaga   43560
gcttgtttta aactcaagta tattaaagac ttgttttca aaatcggtgt gatctgcagc    43620
cgattttcag tcagcatctg ttttttcctt accatccaga tagctcctgt gtccttttcc   43680
cataaccatc catttctgga tggttcaggt aatgaaatta gttccacgtt agtttaata    43740 agagttaatt aggggtcag atgttctata aggaaccag ttcatagtt aattttaaag     43800 ctggattaag tagcttttag tttctgagca ccattatgtt ctcataagca taatattctt   43860
agtaatacta agcaaaaaaa gatgggaagg gggtcagatg gtgattttaa cttgaagtga   43920
caaattccat cctttcctgg cttccattgc aaacttaccc ttgctttcat cctgacatat   43980
```

-continued

```
ggtctccaga gaaatatttt aaataaggta aaccacatgc tgggcaagag agggagtaaa    44040
ccgattaact gggcgctgtt cttccctggg tctcagattc ctcattccta acagagagaa    44100
tttaaactcc atcccttaag ttcctactat cctttagcat tttaagtttg aatccttaat    44160
gtgagtggga aacataacag agaaactgag aaataaatag gatttccttt gcatgatgag    44220
agttctggga caaggtctgc cagacagaac tatactctca cttttcttgt ctgctacttc    44280
ttccacagta tggctatgcc ccaaaaggct catcattggt gttgtatagt gacaagaagt    44340
acaggaacta tcagttcttc gtcgatacag attggcaggg tggcatctat gcttccccaa    44400
ccatcgcagg ctcacggcct ggtggcatta gcgcagcctg ttgggctgcc ttgatgcact    44460
tcggtgagaa cggctatgtt gaagctacca aacagatcat caaaactgct cgcttcctca    44520
agtcagagta tgtgtggaag actggggttc tgccttgtct attgcttttt tgtcctagta    44580
ggctcaaggc acctgcctgg ctaagtatcc atagccctag cccacctgtt gtctcctgcg    44640
atatagaggg cttagggcag cagcttaggg cttaggccag accagctggc ctgggagaag    44700
aagctcccct tctctgccct gacttttgga gggtctttga gacggggcc tcatttgtag    44760 tttatctcat ctctatggat gtcttaataa ctggcagctc ttaccctaag gctaatgtac    44820
aatttaatgg ttaggacagt gattcccaaa cttgagcatg cattctaatc acctgaagga    44880
cttgttaaaa cacaggtagc tgggcccacc cctagagttt ctgattcagt ggaactggga    44940
tgggctctaa aaatttccat ttctggagat actgatgcta ctgctccagg aatcatactt    45000
gaagaatcat tggaataaga aaataattgg aaatgggcca gaaggaatga ggaaaggagg    45060
gcaatgaaat cttgggttaa gccaaggcca gaacaggctg catgctttgt ctaatgtatc    45120
tgttaacatc ttatctgccc atctctctat gtgtcacttg gattggggag gctctttaag    45180
tatattgagg gggaaggaaa gctgcctgca ggcatttctc atttgagaaa gatccttggc    45240
caggcacggt ggctccggcc tgtaatccca gcactttggg aggccaaggc aaaaggatcg    45300
cttcagctca ggaattaaag accaaccgga gcaacatagt gagacattat ctctacaaca    45360
aatttaaaaa ttagccatga ggccgggcgc ggtgactcat ccctgtaatc ccagcacttt    45420
gggaggctga ggcgggtgga tcacctgagg tccagagttc aagaccagcc tgaccaacag    45480
ggagaacccc gtctctacta aaaatacaaa attagccggg cgtggtggcg catgcctgta    45540
atcccagcta ctcaggaggc tgaggcagga gaattgcttg aacccgggag gcagaggttg    45600
cggtgagttg agatggcacc attgcactca agcctgggca acaagaacga aactccatct    45660
caaaaataaa aaataaataa aaataaaaat tagccacatg tggtggtgtg cacctttggt    45720
cccagctaca caggaggctt aaggcaagag gactgcttga acagcccagg aatttgaggt    45780
tacagtgagc tatgatcaca ccactgcact ctagcctggg tgacagagca agaccctgtc    45840
tcaaataaat aagcaaacaa ataaataaaa attagatata tataaaaggt cctcctatag    45900
ctctgatagg gccatttatt aagacctgct ataccatttc ttgctttagg gattacatat    45960
gactttttag aactgtggag atgggcagat tacttttcca gaaattttt tagtacatct    46020 ttcatgcctc agaagcatct aggggaatat aattgggagt tgggtagaca ggttcgaagt    46080
cagtgattga gtcattagat ctagatgggg tttgggcctt ggaattccat ttttattgtt    46140
ccatctatga ttctgatctc agtaagaacc actgatccag tgtagccctc ttctttttg    46200 aagatgagaa gactaaagcc caagggtta gattgcattc attataagga agactttgaa    46260
tgattaaaga gatagtgacc aggggattgt atgtgactga atttactttt tcttccttca    46320 tttattttt tgttttaaga ctggaaaata tcaaaggcat ctttgttttt gggaatcccc    46380
```

-continued

```
aattgtcagt cattgctctg ggatcccgtg attttgacat ctaccgacta tcaaacctga    46440
tgactgctaa ggggtggaac ttgaaccagt tgcagttccc acccaggtaa gcttgaagaa    46500
gcctctttcc cttattttgc tccatgattt tggaagaact tgggtggtac agtaacctga    46560
agtatagagt ttgactgcta gaggctagca cgttagtagc aactgtagta tataaaggat    46620
ttctctcttg ccacctggaa ttattagata caaagaacaa gaccattagc tttaaactct    46680
ggcagaatta ggtgacagcc tcctagacca gtggttggtc atgaggtttt tctctcagtc    46740
tctagccttt ctactctcca atccatcttg tacacagcca tcaaattgct cttataaaat    46800
acttgttacc tggctaatat ttagttcaag atcttcctgg gggtctctaa tcattcaggc    46860
ctgctactgc cttctttatt agactttttct aacctaatct tccatgatgc ctttgagtaa    46920
atgcaccact ccaactgagt acaggtctgt tcatgtcctc tgtgtacagc ttagccttcc    46980
acacgttggt gcattgccag tcccatctgg actatctttt tccctcttca caattccagt    47040 aaacccact aaattcctcc agggcgaggt agaatttctt ctgtgccctg aagtccttta    47100
agaccccagc catgtggccc tgtccccatg agagcacatg ggggctgatt atctaagata    47160
aaagtgtctc attgatggtg acgtggttga aggaatggtg gtggaatttg tgaggggatg    47220
ggtgggacaa agcagccaac actgttcatc ctcttagcat ggttctcagt catgccgaga    47280
agctctgagg ccagcccatg cctgacaccc caagcatgag agagccgaga ttcccaggac    47340
taggaacaac ttggatgact acacttgtca gaaatattgt gaaagggcaa ccaggaaatt    47400
cccgtatttg gggctgcatc attttagaac attttttctt tcttcaaggt tcatctctct    47460
ctgtctcttc tttcctagta ttcatttctg catcacatta ctacacgccc ggaaacgagt    47520
agctatacaa ttcctaaagg acattcgaga atctgtcact caaatcatga agaatcctaa    47580
agcgaagacc acaggaatgg tagggacact tggagttttt tttcttctct tggaaattta    47640
ggtgttggtg gagagtttga aggaatcata tgacccggag tctgttcctg cctctgcccc    47700
tttgccacag acatcttttta tttgttgact ggagctgatg atctctgcat cacccacccc    47760
ttagggttgc tgaagtctca aatgagatac actataaagt accttgtaag ttagagactt    47820
ctgtataaaa gcagctggtg gtagtgtcca tttgaaaaga aaattttgtc acaggaaaga    47880
tagtaaacat gttttttctg gaattttctt aggctagtcc ctttatgcag aaaggcagac    47940
tggaaagtcc ctgtgaaaaa ttgactatgc cagctgtttt tctgatagaa tgatgggatg    48000
ccttaggtgg aaatggggta gggcagtgca catgcgaagc taggactcgg ggagaagggg    48060
ctcattgctg cagtttttatt cttgcttttg gacctggcct cactaataat gtctcttttct    48120 ttggatttgt agggtgccat ctatggcatg cccagacaa ctgttgacag gaatatggtt    48180
gcagaattgt cctcagtctt cttggacagc ttgtacagca ccgacactgt cacccagggc    48240
agccagatga atggttctcc aaaacccac tgaacttgga ccctttctag tctcaagggg    48300
attccagcct tcagaaggtt cttgggatat ggaacaggcc gtgcacaact ttgacatctg    48360
gtcttgctcc atagagcaca actcaagata gaccatgaga cagcttgagc ctcaggattc    48420
ttgttcttcc tcttatcttc cttttgtggt ttttaatttg aagaccccag agaattccat    48480
tacataatga ttttgcccctt gttataaatg ttaccctagg aattgttta accatttcct    48540 tttctaaact ctctagcttt caactttact taaacattgt gtggtagctc tgacctgtcc    48600 tgattctttta gagaagctgg ggtacagttt atgagatagc tagagcttct ttgttatctc    48660
aggcaggagg cgtttacata acagatgttt cctcagctgg gtgtgaggta tactctaagc    48720
```

-continued

```
aggaggcttt tcagccttc tctctctttt tttttttttt tttttttttt gagatggaat    48780
tttgctcttt tgcccagtct ggagtgcagt ggcatgatct cagctcactg caacctccca    48840
cccactgggt tcaagcgatt cttctgcctc agcctcccga gtagctggga ttaccggcac    48900
ccaccaccac gcctggctaa ttttttcaatt ttcttttttca gtagagacgg gttcaccgtg    48960
ttggccaggc tggtcttgaa ctcctgacct caggtgatac cgccccccc gcctcagcct    49020 cccaaagtgc tgggattaca ggcgtgagcc accgtgcctg gccctgtctc tcttaagagt    49080
aggttcattg tctgtcttag agtcacttct attgcaactc attttctttt tccagggcac    49140
agatcgacca agctgccgtt ccctattctg caggacagga ctattctagc atacctgctt    49200
cgtccaccca gcagggttt ggggtggtct cttctgtgcc tgcagtcccc atttgacact    49260
tggttgccac catctttgga gattattgtt tggaatgatg cttccattgg cttttcttg    49320 ttaccatgga ctaggaagaa aacatggtttt ccaaataatc tgggagcttt tggccatggt    49380
gccgccttcc tgaattggca gtggtcagag cacacctgaa ccctatcctg ggctggtgat    49440
gagcagaaat cagaccttt tctatgcttt tttgaatatc agagtaggat gaacacccag    49500
attcaaatat gtcaccaaag ttggtggtgg tccttccctg cacccttgcg ttaagccatt    49560
atgtaatgaa aatgtgtttg cttgaaggaa cagctcaaag caccttcaca gttgccttg    49620 acttacccta ggtgggtgtg aaagagcacc cgtagcaagg aaaattttct ctattagtgt    49680
gttcttctgc ctcttccccc ttgattcagc tttcagaggt actatggcag ttttgcctca    49740
ggtgctgaac atttctcagc cctggctaaa agggagcagc acaggagag aaacaggata    49800 ggaaagcaga atggcgagca gcctatggcc cagggcctgt aatcccttcc caagactagc    49860
tgctcagggt ggtgcaggga caggaccaga ccctgcgcct atttcctgcc ttctttcccc    49920
tatagggaac tctgtaggct gagccactgt cctgctctta tgacattata tcttgtgcct    49980
ttctcctcag cagtgagcag tgagctactc ctggcccagg ccctagggga aatggatcag    50040 tcttttgaggt ttctatttgg ggaggggagt acttaagatg agtcaaaaga cactttcctc    50100
tgttccattc cccatctcag ggactcctga atattcagcc tctccaggct ggtgtcttct    50160
agtttccccc actgggaatg ctggctggga gagccatgac taccagactt tcctcaggc    50220 tccttggcat gttagtctga attgttcttg agcactgtac tactgaccca acaactgtga    50280
ctagctggcc acgccattca gggctggtgt ggcatttatg tgtgtgtgtg tgtgtgtgtg    50340 tgttttttcct gtttgcccag cagtgcattg tgggttccaa gagtgggtag tgtgtgtatg    50400
tgtgtgtgtc agagggagac ctggcaggca cctctttgag agtagctgtg gtcagagctg    50460
tttggtcagt gcattatgtt gaatgaggtc caggaaccca gagccaccca gcagacacca    50520
ctgtggcttg ccagctgcca agatggagaa gcatgtgccc ctgtagagcg tctccccaga    50580
accagacccc gagccactcg cttcctctgt gctgtgacaa cattggtgcc aggggagatg    50640 gtgttttttca aagggaccta ctgtagccac tttaatttac aattaagagc cttagtttga    50700
cttaacactt tgtaggcttt tcattgtgt attttttgtgt atgtgtgcat atagcagcta    50760
ctctgtagca gaggtgggta gagacactta atagtatcat gtcgcatgca gatgtcacat    50820
cggcctctgc aaaaactgta ctgtcttgtt tctgcattag acttaagtag tcatgtgaat    50880
atactgctat gtcactttta atattacgag ttttatactt ggaaaatggt acttgcttct    50940
tttaaatctc tgtcttctct aacctccccc ttcccatttc aatgctccct tcctaatttc    51000
agcaataatc tcaaaaagca attaaatagt taaatgaccc taattgtaat tactgtggat    51060
ggttgcattc atttgattac ttgggcacac acgagatgac aaatggggca gtggccatgc    51120
```

-continued

```
ttgaatgggc tcctggtgag agattgcccc ctggtggtga acaatcgtg tgtgcccact    51180 gataccaaga ccaatgaaag agacacagtt aagcagcaat ccatctcatt tccaggcact    51240
tcaataggtc gctgattggt ccttgcacca gcagtggtag tcgtacctat ttcagagagg    51300
tctgaaattc aggttcttag tttgccaggg acaggcccta tcttatattt ttttccatct    51360
tcatcatcca cttctgctta cagtttgctg cttacaataa cttaatgatg gattgagtta    51420
tctgggtggt ctctagccat ctgggcagtg tggttctgtc taaccaaagg gcattggcct    51480
caaaccctgc atttggttta ggggctaaca gagctcctca gataatcttc acacacatgt    51540
aactgctgga gatcttattc tattatgaat aagaaacgag aagttttcc aaagtgttag     51600 tcaggatctg aaggctgtca ttcagataac ccagcttttc cttttggctt ttagcccatt    51660
cagactttgc cagagtcaag ccaaggattg cttttttgct acagttttct gccaaatggc    51720
ctagttcctg agtacctgga aaccagagag aaagaggatc caggatgtac ttggatgagg    51780
aggcctggct tatctaggaa gtcgtgtctg gggtgcttat tgctgctcca tacagctgta    51840
cgtcagcccc ttggccttct ctgtaggttc ttggcagcaa tgagcagctt tcactcagtg    51900
acacaagtaa ttactgagtc ctaatttgat agccaccaac tgtacctggg taggcaaagt    51960 cagattttg agaaccttt tcctgatttg aagtttaat taccttattt tcttttatgc       52020
tttcctctgt cttgtaatct tttctcttct taatatcctt ccctataatt tcaattattt    52080
ggattaattt tagaataaac ctatttattt ctaaaaaaaa aaagaaaaga aagtgttacc    52140
tgtgtctttg tctcacatga atgtgcttca tacaactgta gtgctgccaa ggttggcttt    52200
attttttgga gacaaggttt cactgtcacc caggctagag ggcaatggca tgatcatcac    52260
tcactgtagc cttgacttcc tgggctcaag tgatcctccc acctcagcct cccgagtagc    52320
tgggaccaca ggtgtgtgcc accatgcctg gctaattttt ctgtatattc tgtagagaca    52380
gagtttctct acattgccca gcctagtctc taactcctga gctcaaatga tcctcccgcc    52440
ttggcctccc aaagtgttgg aaatacaggc atgagctgtc cctgcatcgg gtgaacattt    52500
ttcaacccct gacccatgaa aataagcaga ggcaggaatg taacataaca gcatagtcca    52560
tacctccgca tctggcgtct tctgtccttc agtcctccag tcatcagatc aaagcacact    52620
tggaaaattt taagtcagaa gtggagcaga tgggagacca ctgtctgaat ctcgtttgcc    52680
atcaatatag gtattgataa tccttttacta gcatatatgc taggaacggg gtcctgctaa    52740
tccctcttgt gaacaatacg cttatttctc aacctccagc ctctgcccct ttcctggcct    52800
ttgctggggg accaactcat tcagactgag ttgtgacatg gctagattcc tgttccaagt    52860
gaccccggca tttacaagtc agcttagtac ttgagttagg agacacaggt gagaactatt    52920
aggaagaagg cttcccagtc tctgcatagt gacatatgtg aggtaaaatt tgtgtggcat    52980
tctcgtgggg gtagagatga ggctgctctt agtgccccct tcttcatgac agcgtgggaa    53040
tattctgtcc tagagagttc ctggctgggg aactgactgt gcaaaccatc tcttaactgc    53100
tccagtaata aatagcctgc caggtcctaa gctgcctgtg tcttctctct tgtgggagtaa   53160 accaggcaag ccctaagaac tttgctaaga ttttaagaaa ctgaagagac catcaggatt    53220
tgggatctgc catatctgat atgataggcc tgtgtattat gattctccag agaaacagaa    53280
ccaatacaca caaagagatt tcttataagg aattggctca tgtgattatg gaggctgaca    53340
agtcccaaga tctgtagttg gcaagctgga gaaccaggaa agcagatggt attgttgcac    53400
accggaggct tgtagccttg agacctaagg agagtggatg tttcagttta agtccgaaag    53460
```

-continued

```
caggaaaaga ccaatgtccc acctcaaggc agtcaggcag gaggacttcc ctttatttg      53520 gaagagggtc agccttttt agccttttt ttctgtacag gccttcacct ggttgaatga       53580
ggccacccat gttagggaag acagtcggct ttactcagtc tactgattca aatgttatcc    53640
tcattcagaa acaccctcac agacacaccc ggaatgtttg accaaatgcc tgggcacccc    53700
atggcccaat caagttgaca cctaacatta gccatcacag ccaggaagaa aatataggtt    53760
gagtatccct tatctgaaag gtgtgagacc agaagtgttt cagattttgg attttggaat    53820
atttgcatta tactgacaag ttgagcatct ctaatctgaa aatcagaaat ctaaaatgat    53880
ccaatgagta tttcctttgg gcatcatgtt ggcattcaaa aagtttcaga ttttggattt    53940
ccaattttca aattagggat gttcaacctg taatatggcc ccagactgcc tttctagaca    54000
taggttccac aatgcatata atacctgtgc ccttcacacc cttatctgtg ttcatggtgt    54060
tctctcagcc atctctgcct cccaagaatc ctacccaggt cttcaaggca taactcaaag    54120
cctccagatt tgcccttttc accattaatc acttgcgttc cctttagctc atttcttatc    54180
ctgccaccta gcattaattc actctagtaa tagttaatta gtactagtta attggtaatt    54240
ggtaatagtt aattgtgttc ctgtttgatg ataatcaaat ggtatcccct agatgataat    54300
gaatctgaag gcaaggtggt ctggtccctg tcatttttcca gtaccttgaa cagaggaagt    54360
gcctagcaca gaggaagtgc tttcatttaa atgcctattg actccaattt ggattgacct    54420
gtggaaaaga agtttctaga gcctgagacc aagtgtata atagtttat ttgagacata    54480 aaaacacatg tgtttctatt acatagtgtg gggtttaggg tcctggtttc taagacaaga    54540
ctttatttca ccctgtatca cagcttcctg ggaaatgaat tagggagcaa gagacggcct    54600
ggcaagaaaa tcattattgt tgctgggaag ttgcaaagaa aggggagagt ttattcaaat    54660
tagtgtaaca gagcccccag gatgaagaga gtggtgcagg gaaaaggtct aaattcctgg    54720
tgttggtggg gacactggca catcccacag caaggactca gccctcaacg gcggcggctg    54780
ggtcttggga ggggagtggt gggagggtaa gggctcctca gctccctccc tggactccca    54840
gttcagtcac cccttccccc ggaagaattc aaagaggaag gcagggtct atgtcatgga    54900 cactgctact tgttcgatga agctggccag gtcttcacca cgggg                    54945
```

<210> SEQ ID NO 11
<211> LENGTH: 474
<212> TYPE: DNA
<213> ORGANISM: Homo sapiens
<220> FEATURE:

<400> SEQUENCE: 11

```
gtcgtaagat tcaagacaag ttgaacaaga ccaaggatga tattagcaag aacatgtcat     60
tcctgaaagt ggacaaagag tatgtgaaag ctttaccctc ccagggtctg agctcatctg    120
ctgttttgga gaaacttaag gagtacagct ctatggacgc cttctggcaa gaggggagag    180
cctctggaac agtgtacagt ggggaggaga agctcactga gctccttgtg aaggcttatg    240
gagattttgc atggagtaac cccctgcatc cagatatctt cccaggacta cgcaagatag    300
aggcagaaat tgtgaggata gcttgttccc tgttcaatgg gggaccagat tcgtgtggat    360
gtgtaagtat atgcaagggg catccaatag ccttattttt taggttaaaa tagaagagtt    420
tttaataaat attaattata ttttaaaaaa taaaaatat taaaaataaa aaaa           474
```

<210> SEQ ID NO 12
<211> LENGTH: 670
<212> TYPE: DNA

<213> ORGANISM: Homo sapiens
<220> FEATURE:

<400> SEQUENCE: 12

```
ctagagattt tggaagtata ctcacaaaag ccaagaatta tgtaaatgga cattgcacca      60
agtatgagcc ctggcagcta attgcatgga gtgtcgtgtg gaccctgctg atagtctggg     120
gatatgagtt tgtcttccag ccagagagtt tatggtcaag gtttaaaaag aaatgtttta     180
agctcaccag gaagatgccc attattggtc gtaagattca agacaagttg aacaagacca     240
aggatgatat tagcaagaac atgtcattcc tgaaagtgga caaagagtat gtgaaagctt     300
taccctccca gggtctgagc tcatctgctg ttttggagaa acttaaggag tacagctcta     360
tggacgcctt ctggcaagag gggagagcct ctggaacagt gtacagtggg gaggagaagc     420
tcactgagct ccttgtgaag gcttatggag attttgcatg gagtaacccc ctgcatccag     480
atatcttccc aggactacgc aagatagagg cagaaattgt gaggatagct tgttccctgt     540
tcaatggggg accagattcg tgtggatgtg aagcattgtt tttgttttgt ttttctaata     600
tgttggcgcc atgaaaatca tcatgttcaa atattagtag taataaaggt gatatgcctg     660
gcaaaaaaaa                                                           670
```

<210> SEQ ID NO 13
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 13

```
caggccgcga gacccaggct                                                 20
```

<210> SEQ ID NO 14
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 14

```
ttcagactct cctcacgccg                                                 20
```

<210> SEQ ID NO 15
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 15

```
gtgctaggca tcttcctctt                                                 20
```

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 16

```
caaaggcctt caacatcaga                                                 20
```

<210> SEQ ID NO 17

<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 17
aattcttggc ttttgtggag                                              20

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18
cttggtgcaa tgtccattta                                              20

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
aactcatatc cccagactat                                              20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
taaactctct ggctggaaga                                              20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
gaccataaac tctctggctg                                              20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
tcttcctggt gagcttaaaa                                              20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
ctccataagc cttcacaagg                                                20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
gggaagatat ctggatgcag                                                20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
gaatctggtc ccccattgaa                                                20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
ccagaagtca cacatccaca                                                20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
ttcccccaga agtcacacat                                                20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
ggagttttga tcccttctc                                                 20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
tttctggagt tttgatcccc                                                20

<210> SEQ ID NO 30
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 30
acaatttctg gagttttgat                                                    20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
gggagccaca atttctggag                                                    20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
acaccatgag gaaactgtgg                                                    20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
tttcacccgg aaatcaaatg                                                    20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
acacctttca cccggaaatc                                                    20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
tacttcttgt cactatacaa                                                    20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
ctgccaatct gtatcgacga                                                    20
```

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
atgccaccag gccgtgagcc                                              20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
ctcaccgaag tgcatcaagg                                              20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
ccgttctcac cgaagtgcat                                              20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
catagccgtt ctcaccgaag                                              20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
ttcaacatag ccgttctcac                                              20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
gtagcttcaa catagccgtt                                              20

<210> SEQ ID NO 43
<211> LENGTH: 20
<212> TYPE: DNA
<213> ORGANISM: Artificial Sequence
<220> FEATURE:

```
<223> OTHER INFORMATION: Antisense Oligonucleotide

<400> SEQUENCE: 43
gtttggtagc ttcaacatag                                                  20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
gatctgtttg gtagcttcaa                                                  20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
ttgatgatct gtttggtagc                                                  20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
gagcagtttt gatgatctgt                                                  20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
ggaagcgagc agttttgatg                                                  20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
attttccagt tctgacttga                                                  20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
gctttaggat tcttcatgat                                                  20
```

```
<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
ggcacccatt cctgtggtct                                           20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
tagatggcac ccattcctgt                                           20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
tgccatagat ggcacccatt                                           20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
gggccatgcc atagatggca                                           20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
aaagggtcca agttcagtgg                                           20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
aggctggaat ccccttgaga                                           20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide
```

-continued

```
<400> SEQUENCE: 56
acaagggcaa aatcattatg                                               20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
aaacatctgt tatgtaaacg                                               20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
cactccagac tgggcaaaag                                               20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
gaacctactc ttaagagaga                                               20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
ggcaccatgg ccaaaagctc                                               20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
tcatcaccag cccaggatag                                               20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
agcaaacaca ttttcattac                                               20

<210> SEQ ID NO 63
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 63
cagtggctca gcctacagag                                                    20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
aaagactgat ccatttcccc                                                    20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
gaaagtgtct tttgactcat                                                    20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
cagcacagag gaagcgagtg                                                    20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
ctcccctggc accaatgttg                                                    20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
cctacaaaag tgttaagtca                                                    20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
```

```
ctctgctaca gagtagctgc                                                    20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
tacagttttt gcagaggccg                                                    20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
gggcaatctc tcaccaggag                                                    20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
gtccctggca aactaagaac                                                    20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
accacactgc ccagatggct                                                    20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
aaaaggaaaa gctgggttat                                                    20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
caatccttgg cttgactctg                                                    20

<210> SEQ ID NO 76
<211> LENGTH: 20
<212> TYPE: DNA
<213> ORGANISM: Artificial Sequence
```

<220> FEATURE:
<223> OTHER INFORMATION: Antisense Oligonucleotide

<400> SEQUENCE: 76
ccatttggca gaaaactgta                                                    20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
agccaggcct cctcatccaa                                                    20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
cagtaattac ttgtgtcact                                                    20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
ataggtttat tctaaaatta                                                    20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
aggctacact cctgggcaat                                                    20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
tgtcttgaat ctccaaaggt                                                    20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
gggctgcagg tcccgagccc                                                    20

```
<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
atgagcaaag gatggaccag                                                    20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
gggagccaca ctaaatgaca                                                    20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
cctctcgcac aagggaaagg                                                    20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
cttagctcac cttatgggtg                                                    20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
aaggtgcaca ccaccacatg                                                    20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
attttccagt cttaaaacaa                                                    20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide
```

-continued

```
<400> SEQUENCE: 89
ggatgcccct tgcatatact                                              20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
acatgatgat tttcatggcg                                              20
```

US 6,692,960 B2

ANTISENSE MODULATION OF SPHINGOSINE-1-PHOSPHATE LYASE EXPRESSION

FIELD OF THE INVENTION

The present invention provides compositions and methods for modulating the expression of sphingosine-1-phosphate lyase. In particular, this invention relates to compounds, particularly oligonucleotides, specifically hybridizable with nucleic acids encoding sphingosine-1-phosphate lyase. Such compounds have been shown to modulate the expression of sphingosine-1-phosphate lyase.

BACKGROUND OF THE INVENTION

Sphingolipids are highly enriched in the membranes of most mammalian cells where they were originally thought to play a predominantly structural role as components of the lipid bilayer. It is now appreciated however, that sphingolipid metabolism is a dynamic process and that metabolites of sphingomyelin function as second messengers in cell growth, survival, and death. The dynamic balance between the concentrations of these sphingolipid metabolites and the regulation of opposing signaling pathways, is an important factor that determines whether a cell survives or dies.

Sphingosine-1-phosphate is a phosphorylated derivative of sphingosine, the structural backbone of all sphingolipids, and was initially described as an intermediate in the degradation of long-chain sphingoid bases. However, the discovery that sphingosine-1-phosphate is a potent mitogen for diverse cell types suggested that this metabolite might play other important physiological roles. Sphingosine-1-phosphate has been implicated in a wide variety of biological processes, including mobilization of intracellular calcium, regulation of cytoskeletal organization, as well as cell growth, differentiation, survival, and motility (Spiegel and Milstien, *Biochim. Biophys. Acta,* 2000, 1484, 107–116). Attempts to characterize the mechanisms through which sphingosine-1-phosphate exerts such a broad array of actions have revealed that this sphingolipid metabolite is a member of a new class of lipid second messengers that has both intracellular and extracellular actions (Spiegel and Milstien, *Biochim. Biophys. Acta,* 2000, 1484, 107–116). Since sphingosine-1-phosphate acts as an intracellular messenger, its synthesis should be stimulation-dependent and transient (Yatomi et al., *Prostaglandins,* 2001, 64, 107–122).

Sphingosine-1-phosphate lyase (also known as SPL, SGPL1 and KIAA1252) cleaves sphingosine-1-phosphate into fatty aldehyde and phosphoethanolamine and thus, plays a role in keeping intracellular levels of sphingosine-1-phosphate at low levels (Yatomi et al., *Prostaglandins,* 2001, 64, 107–122). The gene for this enzyme was initially identified in yeast (Saba et al., *J. Biol. Chem.,* 1997, 272, 26087–26090) and the human gene was later cloned and mapped to chromosome 10q20 (Van Veldhoven et al., *Biochim. Biophys. Acta,* 2000, 1487, 128–134). Three different sphingosine-1-phosphate lyase mRNAs of approximately 4.0, 5.8 and 6.7 kb are observed with their highest levels seen in liver and kidney (Van Veldhoven et al., *Biochim. Biophys. Acta,* 2000, 1487, 128–134).

Disclosed and claimed in U.S. Pat. No. 5,187,562 and corresponding PCT publication WO 99/38983 are isolated polynucleotides encoding human sphingosine-1-phosphate lyase and polynucleotides fully complementary to said polynucleotides encoding human sphingosine-1-phosphate lyase (Duckworth et al., 1999; Duckworth et al., 1999).

Disclosed and claimed in PCT publication WO 99/16888 are polynucleotide sequences encoding sphingosine-1-phosphate lyase polypeptides, isolated polynucleotides comprising at least 100 nucleotides complementary to said sphingosine-1-phosphate lyase polynucleotides, pharmaceutical compositions of polynucleotides or antibodies which inhibit the expression of an endogenous sphingosine-1-phosphate lyase gene, and a transgenic animal in which sphingosine-1-phosphatase activity is reduced compared to a wild-type animal (Saba and Zhou, 1999).

Since sphingosine-1-phosphate has been implicated in cell signaling, impaired degradation of this lipid might have severe consequences during neonatal development or even be fatal (Van Veldhoven et al., *Biochim. Biophys. Acta,* 2000, 1487, 128–134).

Sphingosine-1-phosphate has been recently implicated in resistance to the anticancer drug cisplatin and suggestions have been made that manipulating the levels of sphingosine-1-phosphate could be an important therapeutic avenue by potentiating tumor cells to be more sensitive to cisplatin or other drugs (Li et al., *Microbiology,* 2000, 146, 2219–2227).

The synthesis of a small molecule inhibitor of sphingosine-1-phosphate lyase, 2-vinyldihydrosphingosine-1-phosphate, has been reported by Boumendjel et al. (Boumendjel and Miller, *Tetrahedron Lett.,* 1994, 35, 819–822).

Currently, there are no known therapeutic agents that effectively inhibit the synthesis of sphingosine-1-phosphate lyase. To date, investigative strategies aimed at modulating sphingosine-1-phosphate lyase function have involved the use of antibodies and small molecule inhibitors. Consequently, there remains a long felt need for additional agents capable of effectively inhibiting sphingosine-1-phosphate lyase function.

Antisense technology is emerging as an effective means for reducing the expression of specific gene products and may therefore prove to be uniquely useful in a number of therapeutic diagnostic and research applications for the modulation of sphingosine-1-phosphate lyase expression.

The present invention provides compositions and methods for modulating sphingosine-1-phosphate lyase expression, including modulation of alternate mRNA transcripts of sphingosine-1-phosphate lyase.

SUMMARY OF THE INVENTION

The present invention is directed to compounds, particularly antisense oligonucleotides, which are targeted to a nucleic acid encoding sphingosine-1-phosphate lyase, and which modulate the expression of sphingosine-1-phosphate lyase. Pharmaceutical and other compositions comprising the compounds of the invention are also provided. Further provided are methods of modulating the expression of sphingosine-1-phosphate lyase in cells or tissues comprising contacting said cells or tissues with one or more of the antisense compounds or compositions of the invention. Further provided are methods of treating an animal, particularly a human, suspected of having or being prone to a disease or condition associated with expression of sphingosine-1-phosphate lyase by administering a therapeutically or prophylactically effective amount of one or more of the antisense compounds or compositions of the invention.

DETAILED DESCRIPTION OF THE INVENTION

The present invention employs oligomeric compounds, particularly antisense oligonucleotides, for use in modulating the function of nucleic acid molecules encoding sphingosine-1-phosphate lyase, ultimately modulating the amount of sphingosine-1-phosphate lyase produced. This is accomplished by providing antisense compounds which specifically hybridize with one or more nucleic acids encoding sphingosine-1-phosphate lyase. As used herein, the terms "target nucleic acid" and "nucleic acid encoding sphingosine-1-phosphate lyase" encompass DNA encoding sphingosine-1-phosphate lyase, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of sphingosine-1-phosphate lyase. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding sphingosine-1-phosphate lyase. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding sphingosine-1-phosphate lyase, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5' UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3' UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'—5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation, and the sequences of these compounds are hereinbelow identified as preferred embodiments of the invention. The target sites to which these preferred sequences are complementary are hereinbelow referred to as "active sites" and are therefore preferred sites for targeting. Therefore another embodiment of the invention encompasses compounds which hybridize to these active sites.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds of the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17–24; Celis, et al., *FEBS Lett.*, 2000, 480, 2–16), SAGE (serial analysis of gene expression) (Madden, et al., *Drug Discov. Today*, 2000, 5, 415–425), READS (restriction enzyme amplification of digested cDNAs) (Prashar and Weissman, *Methods Enzymol.*, 1999, 303, 258–72), TOGA (total gene expression analysis) (Sutcliffe, et al., *Proc. Natl. Acad. Sci. U.S. A.*, 2000, 97, 1976–81), protein arrays and proteomics (Celis, et al., *FEBS Lett.*, 2000, 480, 2–16; Jungblut, et al., *Electrophoresis*, 1999, 20, 2100–10), expressed sequence tag (EST) sequencing (Celis, et al., *FEBS Lett.*, 2000, 480, 2–16; Larsson, et al., *J. Biotechnol.*, 2000, 80, 143–57), subtractive RNA fingerprinting (SuRF) (Fuchs, et al., *Anal. Biochem.*, 2000, 286, 91–98; Larson, et al., *Cytometry*, 2000, 41, 203–208), subtractive cloning, differential display (DD) (Jurecic and Belmont, *Curr. Opin. Microbiol.*, 2000, 3, 316–21), comparative genomic hybridization (Carulli, et al., *J. Cell Biochem. Suppl.*, 1998, 31, 286–96), FISH (fluorescent in situ hybridization) techniques (Going and Gusterson, *Eur. J. Cancer*, 1999, 35, 1895–904) and mass spectrometry methods (reviewed in (To, *Comb. Chem. High Throughput Screen*, 2000, 3, 235–41).

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'–5' linkages, 2'–5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497–1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$H_2$, O($CH_2$)$_n$$CH_3$, O($CH_2$)$_n$ON$H_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486–504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$)$_2$, also described in examples hereinbelow.

A further prefered modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—CH$_2$—)$_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'-O—CH$_3$), 2'-aminopropoxy (2'-OCH$_2$CH$_2$CH$_2$NH$_2$), 2'-allyl (2'-CH$_2$—CH=CH$_2$), 2'-O-allyl (2'-O—CH$_2$—CH=CH$_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'–5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b] [1,4]benzothiazin-2(3H)-one), G-clamps such as a substituted phenoxazine cytidine (e.g. 9-(2-aminoethoxy)-H-pyrimido[5,4-b] [1,4] benzoxazin-2(3H)-one), carbazole cytidine (2H-pyrimido[4,5-b]indol-2-one), pyridoindole cytidine (H-pyrido[3',2':4,5] pyrrolo[2,3-d]pyrimidin-2-one). Modified nucleobases may also include those in which the purine or pyrimidine base is replaced with other heterocycles, for example 7-deazaadenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289–302, Crooke, S. T. and Lebleu, B. ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds.,*Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121, 5,596,091; 5,614,617; 5,645,985; 5,830,653; 5,763, 588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA*, 1989, 86, 6553–6556), cholic acid (Manoharan et al., *Bioorg. Med. Chem. Let.*, 1994, 4, 1053–1060), a thioether, e.g., hexyl-S-tritylthiol (Manoharan et al.,*Ann. N.Y. Acad. Sci.*, 1992, 660, 306–309; Manoharan et al., *Bioorg. Med. Chem. Let.*, 1993, 3, 2765–2770), a thiocholesterol (Oberhauser et al., *Nucl. Acids Res.*, 1992, 20, 533–538), an aliphatic chain, e.g., dodecandiol or undecyl residues (Saison-Behmoaras et al., *EMBO J.*, 1991, 10, 1111–1118; Kabanov et al., *FEBS Lett.*, 1990, 259, 327–330; Svinarchuk et al., *Biochimie*, 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651–3654; Shea et al., *Nucl. Acids Res.*, 1990, 18, 3777–3783), a polyamine or a polyethylene glycol chain (Manoharan et al., *Nucleosides & Nucleotides*, 1995, 14, 969–973), or adamantane acetic acid (Manoharan et al., *Tetrahedron Lett.*, 1995, 36, 3651–3654), a palmityl moiety (Mishra et al., *Biochim. Biophys. Acta*, 1995, 1264, 229–237), or an octadecylamine or hexylamino-carbonyl-oxycholesterol moiety (Crooke et al., *J. Pharmacol. Exp. Ther.*, 1996, 277, 923–937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.,* 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of sphingosine-1-phosphate lyase is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding sphingosine-1-phosphate lyase, enabling sandwich and other assays to easily be constructed to exploit this fact. Hybridization of the antisense oligonucleotides of the invention with a nucleic acid encoding sphingosine-1-phosphate lyase can be detected by means known in the art. Such means may include conjugation of an enzyme to the oligonucleotide, radiolabelling of the oligonucleotide or any other suitable detection means. Kits using such detection means for detecting the level of sphingosine-1-phosphate lyase in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Prefered bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate. Prefered fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also prefered are combinations of penetration enhancers, for example, fatty acids/salts in combination with bile acids/salts. A particularly prefered combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylamino-methylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. application Ser Nos. 08/886,829 (filed Jul. 1, 1997), 09/108,673 (filed Jul. 1, 1998), 09/256,515 (filed Feb. 23, 1999), 09/082,624 (filed May 21, 1998) and 09/315,298 (filed May 20, 1999) each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 μm in diameter. (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and tri-glycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385–1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.,* 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release,* 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting,* 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research,* 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S. T. P. Pharma. Sci.,* 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters,* 1987, 223, 42; Wu et al., *Cancer Research,* 1993, 53, 3765).

Various liposomes comprising one or more glycolipids are known in the art. Papahadjopoulos et al. (*Ann. N.Y. Acad. Sci.,* 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.,* 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.,* 1980, 53, 2778) described liposomes comprising a nonionic detergent, $2C_{12}15G$, that contains a PEG moiety. Illum et al. (*FEBS Lett.,* 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.,* 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta,* 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. Nos. 5,540,935 (Miyazaki et al.) and 5,556,948 (Tagawa et al.)

describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems*, 1991, p. 92); and perfluorochemical emulsions, such as FC-43. Takahashi et al., *J. Pharm. Pharmacol.*, 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems*, 1991, p.92; Muranishi, *Critical Reviews in Therapeutic Drug Carrier Systems*, 1990, 7, 1–33; El Hariri et al., *J. Pharm. Pharmacol.*, 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics*, 9th Ed., Hardman et al. Eds., McGraw-Hill, N.Y., 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems,* 1991, page 92; Swinyard, Chapter 39 In: *Remington's Pharmaceutical Sciences,* 18th Ed., Gennaro, ed., Mack Publishing Co., Easton, Pa., 1990, pages 782–783; Muranishi, *Critical Reviews in Therapeutic Drug Carrier Systems,* 1990, 7, 1–33; Yamamoto et al., *J. Pharm. Exp. Ther.,* 1992, 263, 25; Yamashita et al., *J. Pharm. Sci.,* 1990, 79, 579–583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.,* 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems,* 1991, page 92; Muranishi, *Critical Reviews in Therapeutic Drug Carrier Systems,* 1990, 7, 1–33; Buur et al., *J. Control Rel.,* 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems,* 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems,* 1991, page 92); and non-steroidal anti-inflammatory agents such as diclofenac sodium, indomethacin and phenylbutazone (Yamashita et al., *J. Pharm. Pharmacol.,* 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4' isothiocyano-stilbene-2,2'-disulfonic acid (Miyao et al., *Antisense Res. Dev.,* 1995, 5, 115–121; Takakura et al., *Antisense & Nucl. Acid Drug Dev.,* 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy,* 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy,* 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-alkoxy Amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods [Sanghvi, et. al., *Nucleic Acids Research,* 1993, 21, 3197–3203] using commercially available phosphoramidites (Glen Research, Sterling Va. or ChemGenes, Needham Mass.).

2'-Fluoro Amidites

2'-Fluorodeoxyadenosine Amidites

2'-fluoro oligonucleotides were synthesized as described previously [Kawasaki, et. al., *J. Med. Chem.,* 1993, 36, 831–841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanine. Deprotection of the TPDS group was followed by protection of the hydroxyl group with THP to give diisobutyryl di-THP protected arabino-furanosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3' phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3' phosphoramidites.

2'-O-(2-Methoxyethyl) Modified Amidites

2'-O-Methoxyethyl-substituted nucleoside amidites are prepared as follows, or alternatively, as per the methods of Martin, P., *Helvetica Chimica Acta*, 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/hexane(4:1). Pure product fractions were evaporated to yield 96 g (84%). An additional 1.5 g was recovered from later fractions.

3',-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSo_4$ and evaporated to give a residue (96 g). The residue was chromatographed on a 1.5 kg silica column using EtOAc/hexane (1:1) containing 0.5% $Et_3NH$ as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite

N4-Benzoyl-2'-O-methoxyethyl-5'-O-dimethoxytrityl-5-methylcytidine (74 g, 0.10 M) was dissolved in $CH_2Cl_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl) Nucleoside Amidites and 2'-O-(dimethylaminooxyethyl) Nucleoside Amidites 2'-(Dimethylaminooxyethoxy) nucleoside amidites 2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-$O^2$-2'-anhydro-5-methyluridine $O^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring, tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-$O^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure <100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5',-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy) ethyl]-5-methyluridine

2'-O-([2-phthalimidoxy)ethyl]-5'-t-butyldiphenylsilyl-5-methyluridine (3.1 g, 4.5 mmol) was dissolved in dry CH$_2$Cl$_2$ (4.5 mL) and methylhydrazine (300 mL, 4.64 mmol) was added dropwise at −10° C. to 0° C. After 1 h the mixture was filtered, the filtrate was washed with ice cold CH$_2$Cl$_2$ and the combined organic phase was washed with water, brine and dried over anhydrous Na$_2$SO$_4$. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was strirred for 1 h. Solvent was removed under vacuum; residue chromatographed to get 5'-O-tert-butyldiphenylsilyl-2'-O-[(2-formadoximinooxy) ethyl]-5-methyluridine as white foam (1.95 g, 78%).

5'-O-tert-Butyldiphenylsilyl-2'-O-[N,N-dimethylaminooxyethyl]-5-methyluridine

5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in CH$_2$Cl$_2$). Aqueous NaHCO$_3$ solution (5%, 10 mL) was added and extracted with ethyl acetate (2×20 mL). Ethyl acetate phase was dried over anhydrous Na$_2$SO$_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% NaHCO$_3$ (25 mL) solution was added and extracted with ethyl acetate (2×25 mL). Ethyl acetate layer was dried over anhydrous Na$_2$SO$_4$ and evaporated to dryness. The residue obtained was purified by flash column chromatography and eluted with 5% MeOH in CH$_2$Cl$_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in CH$_2$Cl$_2$). Solvent was removed under vacuum and the residue placed on a flash column and eluted with 10% MeOH in CH$_2$Cl$_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over P$_2$O$_5$ under high vacuum overnight at 40° C. It was then co-evaporated with anhydrous pyridine (20 mL). The residue obtained was dissolved in pyridine (11 ml) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in CH$_2$Cl$_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over P$_2$O$_5$ under high vacuum overnight at 40° C. Then the reaction mixture was dissolved in anhydrous acetonitrile (8.4 mL) and 2-cyanoethyl-N,N,N$^1$,N$^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous NaHCO$_3$ (40 mL). Ethyl acetate layer was dried over anhydrous Na$_2$SO$_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) Nucleoside Amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-hydroxyethyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-([2-phthalmidoxy]ethyl)-5'-O-(4,4'-dimethoxytrityl)guanosine-3'-[(2-cyanoethyl)-N,N-diisopropylphosphoramidite].

2'-dimethylaminoethoxyethoxy (2'-DMAEOE) Nucleoside Amidites

2'-dimethylaminoethoxyethoxy nucleoside amidites (also known in the art as 2'-O-dimethylaminoethoxyethyl, i.e., 2'-O—CH$_2$—O—CH$_2$—N(CH$_3$)$_2$, or 2'-DMAEOE nucleoside amidites) are prepared as follows. Other nucleoside amidites are prepared similarly.

2'-O-[2(2-N,N-dimethylaminoethoxy)ethyl]-5-methyl Uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. O—,2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethylaminoethoxy) ethyl)]-5-methyl Uridine To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with $CH_2Cl_2$ (2×200 mL). The combined $CH_2Cl_2$ layers are washed with saturated $NaHCO_3$ solution, followed by saturated NaCl solution and dried over anhydrous sodium sulfate. Evaporation of the solvent followed by silica gel chromatography using MeOH:$CH_2Cl_2$:$Et_3$N (20:1, v/v, with 1% triethylamine) gives the title compound.

5'-O-Dimethoxytrityl-2'-O-[2(2-N,N-dimethylaminoethoxy)-ethyl)]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in $CH_2Cl_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3',-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethyl-hydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]—[2'-deoxy]—[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]—[2'-deoxy]—[2'-O-(Methoxyethyl)] Chimeric Phosphorothioate Oligonucleotides

[2'-O-(2-methoxyethyl)]—[2'-deoxy]—[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]—[2'-deoxy Phosphorothioate]—[2'-O-(2-Methoxyethyl) Phosphodiester] Chimeric Oligonucleotides

[2'-O-(2-methoxyethyl phosphodiester]—[2'-deoxy phosphorothioate]—[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$p nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated NH OH at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8

Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following 4 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence.

NHDF cells:

Human neonatal dermal fibroblast (NHDF) were obtained from the Clonetics Corporation (Walkersville Md.). NHDFs were routinely maintained in Fibroblast Growth Medium (Clonetics Corporation, Walkersville Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville Md.). HEKs were routinely maintained in Keratinocyte Growth Medium (Clonetics Corporation, Walkersville Md.) formulated as recommended by the supplier. Cells were routinely maintained for up to 10 passages as recommended by the supplier.

Treatment With Antisense Compounds:

When cells reached 80% confluency, they were treated with oligonucleotide. For cells grown in 96-well plates, wells were washed once with 200 μL OPTI-MEM™-1 reduced-serum medium (Gibco BRL) and then treated with 130 μL of OPTI-MEM™-1 containing 3.75 μg/mL LIPO-FECTIN T (Gibco BRL) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of Oligonucleotide Inhibition of sphingosine-1-phosphate Lyase Expression Antisense modulation of sphingosine-1-phosphate lyase expression can be assayed in a variety of ways known in the art. For example, sphingosine-1-phosphate lyase mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+mRNA. Methods of RNA isolation are taught in, for example, Ausubel, F. M. et al., *Current Protocols in Molecular Biology*, Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of sphingosine-1-phosphate lyase can be quantitated in a variety of ways well known in the art, such as immunoprecipitation, Western blot analysis (immunoblotting), ELISA or fluorescence-activated cell sorting (FACS). Antibodies directed to sphingosine-1-phosphate lyase can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1–11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1–11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1–10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1–10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1–11.2.22, John Wiley & Sons, Inc., 1991.

Example 11

Poly(A)+mRNA Isolation

Poly(A)+mRNA was isolated according to Miura et al., *Clin. Chem.*, 1996, 42, 1758–1764. Other methods for poly(A)+mRNA isolation are taught in, for example, Ausubel, F. M. et al., *Current Protocols in Molecular Biology*, Volume 1, pp. 4.5.1–4.5.3, John Wiley & Sons, Inc., 1993. Briefly, for cells grown on 96-well plates, growth medium was removed from the cells and each well was washed with 200 μL cold PBS. 60 μL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 μL of lysate was transferred to Oligo d(T) coated 96-well plates (AGCT Inc., Irvine Calif.). Plates were incubated for 60 minutes at room temperature, washed 3 times with 200 μL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 μL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total RNA was isolated using an RNEASY 96™ kit and buffers purchased from Qiagen Inc. (Valencia Calif.) following the manufacturer's recommended procedures. Briefly, for cells grown on 96-well plates, growth medium was removed from the cells and each well was washed with 200 μL cold PBS. 100 μL Buffer RLT was added to each well and the plate vigorously agitated for 20 seconds. 100 μL of 70% ethanol was then added to each well and the contents mixed by pipetting three times up and down. The samples were then transferred to the RNEASY $_{96}$™ well plate attached to a QIAVAC™ manifold fitted with a waste collection tray and attached to a vacuum source. Vacuum was applied for 15 seconds. 1 mL of Buffer RW1 was added to each well of the RNEASY 96™ plate and the vacuum again applied for 15 seconds. 1 mL of Buffer RPE was then added to each well of the RNEASY 96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 μL water into each well, incubating 1 minute, and then applying the vacuum for 30 seconds. The elution step was repeated with an additional 60 μL water.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-Time Quantitative PCR Analysis of Sphingosine-1-phosphate Lyase mRNA Levels Quantitation of sphingosine-1-phosphate lyase mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from PE-Applied Biosystems, Foster City, Calif. RT-PCR reactions were carried out by adding 25 μL PCR cocktail (1×TAQMAN™ buffer A, 5.5 mM $MgCl_2$, 300 μM each of dATP, dCTP and dGTP, 600 μM of dUTP, 100 nM each of forward primer, reverse primer, and probe, 20 Units RNAse inhibitor, 1.25 Units AMPLITAQ GOLD™, and 12.5 Units MuLV reverse transcriptase) to 96 well plates containing 25 μL total RNA solution. The RT reaction was carried out by incubation for 30 minutes at 48° C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones, L. J., et al, *Analytical Biochemistry*, 1998, 265, 368–374.

In this assay, 175 μL of RiboGreen working reagent (RiboGreen™ reagent diluted 1:2865 in 10 mM Tris-HCl, 1 mM EDTA, pH 7.5) is pipetted into a 96-well plate containing 25 uL purified, cellular RNA. The plate is read in a CytoFluor 4000 (PE Applied Biosystems) with excitation at 480 nm and emission at 520 nm.

Probes and primers to human sphingosine-1-phosphate lyase were designed to hybridize to a human sphingosine-1-phosphate lyase sequence, using published sequence information (GenBank accession number AB033078, incorporated herein as SEQ ID NO:3). For human sphingosine-1-phosphate lyase the PCR primers were:

forward primer:
AGTAACCCCCTGCATCCAGAT (SEQ ID NO:4)

reverse primer:
GAACAGGGAACAAGCTATCCTCA (SEQ ID NO:5)

the PCR probe was: FAM-TCCCAGGACTACGCAAGATAGAGGCAGA-TAMRA (SEQ ID NO: 6) where FAM (PE-Applied Biosystems, Foster City, Calif.) is the fluorescent reporter dye) and TAMRA (PE-Applied Biosystems, Foster City, Calif.) is the quencher dye. For human GAPDH the PCR primers were:

forward primer:
GAAGGTGAAGGTCGGAGTC (SEQ ID NO:7)

reverse primer:
GAAGATGGTGATGGGATTTC (SEQ ID NO:8)

PCR probe was: 5' JOE-CAAGCTTCCCGTTCTCAGCC-TAMRA 3' (SEQ ID NO: 9) where JOE (PE-Applied Biosystems, Foster City, Calif.) is the fluorescent reporter dye) and TAMRA (PE-Applied Biosystems, Foster City, Calif.) is the quencher dye.

Example 14
Northern Blot Analysis of sphingosine-1-phosphate Lyase mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human sphingosine-1-phosphate lyase, a human sphingosine-1-phosphate lyase specific probe was prepared by PCR using the forward primer AGTAACCCCCTG-CATCCAGAT (SEQ ID NO: 4) and the reverse primer GAACAGGGAACAAGCTATCCTCA (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15
Antisense Inhibition of Human sphingosine-1-phosphate Lyase Expression by Chimeric Phosphorothioate Oligonucleotides Having 2'-MOE Wings and a Deoxy Gap In accordance with the present invention, a series of oligonucleotides were designed to target different regions of the human sphingosine-1-phosphate lyase RNA, using published sequences (GenBank accession number AB033078, incorporated herein as SEQ ID NO: 3, a genomic sequence assembled from GenBank accession numbers AC023639.2 and AC069538.2, incorporated herein as SEQ ID NO: 10, GenBank accession number AI128825, the complement of which is incorporated herein as SEQ ID NO: 11, and GenBank accession number AI701419, the complement of which is incorporated herein as SEQ ID NO: 12). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human sphingosine-1-phosphate lyase mRNA levels by quantitative real-time PCR as described in other examples herein. Data are averages from two experiments. If present, "N.D." indicates "no data".

TABLE 1

Inhibition of human sphingosine-1-phosphate lyase mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 146215 | 5' UTR | 3 | 47 | caggccgcgagacccaggct | 73 | 13 |
| 146216 | 5' UTR | 3 | 146 | ttcagactctcctcacgccg | 0 | 14 |
| 146217 | 5' UTR | 3 | 192 | gtgctaggcatcttcctctt | 74 | 15 |
| 146218 | Exon 2: Exon 3 | 3 | 218 | caaaggccttcaacatcaga | 47 | 16 |
| 146219 | Exon 3 | 3 | 266 | aattcttggcttttgtggag | 37 | 17 |
| 146220 | Exon 3 | 3 | 289 | cttggtgcaatgtccattta | 77 | 18 |
| 146221 | Exon 3 | 3 | 357 | aactcatatccccagactat | 81 | 19 |
| 146222 | Exon 3 | 3 | 379 | taaactctctggctggaaga | 77 | 20 |
| 146223 | Exon 3: Exon 4 | 3 | 384 | gaccataaactctctggctg | 71 | 21 |
| 146224 | Exon 4 | 3 | 422 | tcttcctggtgagcttaaaa | 67 | 22 |

TABLE 1-continued

Inhibition of human sphingosine-1-phosphate lyase mRNA levels
by chimeric phosphorothioate oligonucleotides having 2'-MOE
wings and a deoxy gap

| ISIS # | REGION | TARGET SEQ ID NO | TARGET SITE | SEQUENCE | % INHIB | SEQ ID NO |
|---|---|---|---|---|---|---|
| 146225 | Exon 6: Exon 7 | 3 | 677 | ctccataagccttcacaagg | 5 | 23 |
| 146226 | Exon 7 | 3 | 717 | gggaagatatctggatgcag | 17 | 24 |
| 146227 | Exon 7 | 3 | 786 | gaatctggtcccccattgaa | 25 | 25 |
| 146228 | Exon 7: Exon 8 | 3 | 807 | ccagaagtcacacatccaca | 59 | 26 |
| 146229 | Exon 7: Exon 8 | 3 | 812 | ttcccccagaagtcacacat | 67 | 27 |
| 146230 | Exon 8 | 3 | 879 | ggagttttgatcccttctc | 66 | 28 |
| 146231 | Exon 8: Exon 9 | 3 | 884 | tttctggagttttgatcccc | 62 | 29 |
| 146232 | Exon 8: Exon 9 | 3 | 888 | acaatttctggagttttgat | 28 | 30 |
| 146233 | Exon 8: Exon 9 | 3 | 895 | gggagccacaatttctggag | 0 | 31 |
| 146234 | Exon 10 | 3 | 1062 | acaccatgaggaaactgtgg | 9 | 32 |
| 146235 | Exon 11 | 3 | 1207 | tttcacccggaaatcaaatg | 67 | 33 |
| 146236 | Exon 11 | 3 | 1212 | acaccttcacccggaaatc | 0 | 34 |
| 146237 | Exon 12 | 3 | 1293 | tacttcttgtcactatacaa | 67 | 35 |
| 146238 | Exon 12 | 3 | 1330 | ctgccaatctgtatcgacga | 81 | 36 |
| 146239 | Exon 12 | 3 | 1380 | atgccaccaggccgtgagcc | 57 | 37 |
| 146240 | Exon 12 | 3 | 1420 | ctcaccgaagtgcatcaagg | 60 | 38 |
| 146241 | Exon 12 | 3 | 1425 | ccgttctcaccgaagtgcat | 72 | 39 |
| 146242 | Exon 12 | 3 | 1430 | catagccgttctcaccgaag | 0 | 40 |
| 146243 | Exon 12 | 3 | 1435 | ttcaacatagccgttctcac | 82 | 41 |
| 146244 | Exon 12 | 3 | 1440 | gtagcttcaacatagccgtt | 64 | 42 |
| 146245 | Exon 12 | 3 | 1445 | gtttggtagcttcaacatag | 56 | 43 |
| 146246 | Exon 12 | 3 | 1450 | gatctgtttggtagcttcaa | 78 | 44 |
| 146247 | Exon 12 | 3 | 1455 | ttgatgatctgtttggtagc | 67 | 45 |
| 146248 | Exon 12 | 3 | 1463 | gagcagttttgatgatctgt | 66 | 46 |
| 146249 | Exon 12 | 3 | 1469 | ggaagcgagcagttttgatg | 61 | 47 |
| 146250 | Exon 12: Exon 13 | 3 | 1489 | attttccagttctgacttga | 73 | 48 |
| 146251 | Exon 14 | 3 | 1731 | gctttaggattcttcatgat | 68 | 49 |
| 146252 | Exon 14 | 3 | 1753 | ggcacccattcctgtggtct | 61 | 50 |
| 146253 | Exon 14: Exon 15 | 3 | 1758 | tagatggcacccattcctgt | 67 | 51 |
| 146254 | Exon 14: Exon 15 | 3 | 1763 | tgccatagatggcacccatt | 52 | 52 |
| 146255 | Exon 15 | 3 | 1769 | gggccatgccatagatggca | 26 | 53 |
| 146256 | Stop Codon | 3 | 1901 | aaagggtccaagttcagtgg | 34 | 54 |
| 146257 | 3' UTR | 3 | 1925 | aggctggaatccccttgaga | 66 | 55 |
| 146258 | 3' UTR | 3 | 2117 | acaagggcaaaatcattatg | 0 | 56 |
| 146259 | 3' UTR | 3 | 2305 | aaacatctgttatgtaaacg | 0 | 57 |
| 146260 | 3' UTR | 3 | 2419 | cactccagactgggcaaaag | 55 | 58 |
| 146261 | 3' UTR | 3 | 2698 | gaacctactcttaagagaga | 42 | 59 |
| 146262 | 3' UTR | 3 | 2995 | ggcaccatggccaaaagctc | 59 | 60 |
| 146263 | 3' UTR | 3 | 3054 | tcatcaccagcccaggataq | 0 | 61 |
| 146264 | 3' UTR | 3 | 3194 | agcaaacacattttcattac | 0 | 62 |
| 146265 | 3' UTR | 3 | 3561 | cagtggctcagcctacagag | 46 | 63 |
| 146266 | 3' UTR | 3 | 3657 | aaagactgatccatttcccc | 65 | 64 |
| 146267 | 3' UTR | 3 | 3709 | gaaagtgtcttttgactcat | 66 | 65 |
| 146268 | 3' UTR | 3 | 4224 | cagcacagaggaagcgagtg | 60 | 66 |
| 146269 | 3' UTR | 3 | 4247 | ctcccctggcaccaatgttg | 56 | 67 |
| 146270 | 3' UTR | 3 | 4327 | cctacaaaagtgttaagtca | 61 | 68 |
| 146271 | 3' UTR | 3 | 4383 | ctctgctacagagtagctgc | 0 | 69 |
| 146272 | 3' UTR | 3 | 4450 | tacagtttttgcagaggccg | 0 | 70 |
| 146273 | 3' UTR | 3 | 4759 | gggcaatctctcaccaggag | 3 | 71 |
| 146274 | 3' UTR | 3 | 4942 | gtccctggcaaactaagaac | 52 | 72 |
| 146275 | 3' UTR | 3 | 5064 | accacactgcccagatggct | 65 | 73 |
| 146276 | 3' UTR | 3 | 5255 | aaaaggaaaagctgggttat | 42 | 74 |
| 146277 | 3' UTR | 3 | 5300 | caatccttggcttgactctg | 6 | 75 |
| 146278 | 3' UTR | 3 | 5329 | ccatttggcagaaaactgta | 12 | 76 |
| 146279 | 3' UTR | 3 | 5400 | agccaggcctcctcatccaa | 73 | 77 |
| 146280 | 3' UTR | 3 | 5526 | cagtaattacttgtgtcact | 41 | 78 |
| 146281 | 3' UTR | 3 | 5714 | ataggtttattctaaaatta | 57 | 79 |
| 146282 | Intron 4 | 10 | 24194 | aggctacactcctgggcaat | 51 | 80 |
| 146283 | Intron 4: Exon 5 | 10 | 25709 | tgtcttgaatctccaaaggt | 71 | 81 |
| 146284 | Intron 7 | 10 | 32823 | gggctgcaggtcccgagccc | 54 | 82 |
| 146285 | Intron 7 | 10 | 34839 | atgagcaaaggatggaccag | 0 | 83 |

TABLE 1-continued

Inhibition of human sphingosine-1-phosphate lyase mRNA levels
by chimeric phosphorothioate oligonucleotides having 2'-MOE
wings and a deoxy gap

| ISIS # | REGION | TARGET SEQ ID NO | TARGET SITE | SEQUENCE | % INHIB | SEQ ID NO |
|---|---|---|---|---|---|---|
| 146286 | Intron 8: Exon 9 | 10 | 40720 | gggagccacactaaatgaca | 78 | 84 |
| 146287 | Intron 10 | 10 | 42463 | cctctcgcacaagggaaagg | 64 | 85 |
| 146288 | Exon 11: Intron 11 | 10 | 42915 | cttagctcaccttatgggtg | 1 | 86 |
| 146289 | Intron 12 | 10 | 45697 | aaggtgcacaccaccacatg | 58 | 87 |
| 146290 | Intron 12: Exon 13 | 10 | 46330 | attttccagtcttaaaacaa | 9 | 88 |
| 146291 | Intron 7 | 11 | 366 | ggatgcccttgcatatact | 40 | 89 |
| 146292 | Exon 7b | 12 | 607 | acatgatgattttcatggcg | 12 | 90 |

As shown in Table 1, SEQ ID NOs 13, 15, 16, 18, 19, 20, 21, 22, 26, 27, 28, 29, 33, 35, 36, 37, 38, 39, 41, 42, 43, 44, 45, 46, 47, 48, 49, 50, 51, 52, 55, 58, 59, 60, 63, 64, 65, 66, 67, 68, 72, 73, 74, 77, 78, 79, 80, 81, 82, 84, 85, 87 and 89 demonstrated at least 40% inhibition of human sphingosine-1-phosphate lyase expression in this assay and are therefore preferred. The target sites to which these preferred sequences are complementary are herein referred to as "active sites" and are therefore preferred sites for targeting by compounds of the present invention.

Example 16
Western Blot Analysis of sphingosine-1-phosphate Lyase Levels

Western blot analysis (immunoblot analysis) is carried out using standard methods. Cells are harvested 16–20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to sphingosine-1-phosphate lyase is used, with a radiolabelled or fluorescently labeled secondary antibody directed against the primary antibody species. Bands are visualized using a PHOSPHORIMAGER™ (Molecular Dynamics, Sunnyvale Calif.).

What is claimed is:

1. A compound up to 50 nucleobases in length comprising at least an 8-nucleobase portion of SEQ ID NO: 13, 15, 16, 18, 19, 20, 21, 22, 26, 28, 29, 33, 35, 36, 37, 38, 39, 41, 42, 43, 44, 45, 46, 47, 48, 49, 50, 51, 52, 58, 59, 60, 63, 64, 65, 66, 67, 68, 72, 73, 74, 77, 78, 79, 80, 81, 82, 84, 85, 87 or 89 which inhibits the expression of sphingosine-1-phosphate lyase.

2. The compound of claim 1 which is an antisense oligonucleotide.

3. The compound of claim 2 wherein the antisense oligonucleotide comprises at least one modified internucleoside linkage.

4. The compound of claim 3 wherein the modified internucleoside linkage is a phosphorothioate linkage.

5. The compound of claim 2 wherein the antisense oligonucleotide comprises at least one modified sugar moiety.

6. The compound of claim 5 wherein the modified sugar moiety is a 2'-O-methoxyethyl sugar moiety.

7. The compound of claim 2 wherein the antisense oligonucleotide comprises at least one modified nucleobase.

8. The compound of claim 7 wherein the modified nucleobase is a 5-methylcytosine.

9. The compound of claim 2 wherein the antisense oligonucleotide is a chimeric oligonucleotide.

10. A composition comprising the compound of claim 1 and a pharmaceutically acceptable carrier or diluent.

11. The composition of claim 10 further comprising a colloidal dispersion system.

12. The composition of claim 10 wherein the compound is an antisense oligonucleotide.

13. A method of inhibiting the expression of sphingosine-1-phosphate lyase in cells or tissues comprising contacting said cells or tissues in vitro with the compound of claim 1 so that expression of sphingosine-1-phosphate lyase is inhibited.

14. A compound consisting of SEQ ID NO: 27 or 55.

* * * * *

UNITED STATES PATENT AND TRADEMARK OFFICE
CERTIFICATE OF CORRECTION

PATENT NO. : 6,692,960 B2
DATED : February 17, 2004
INVENTOR(S) : C. Frank Bennett et al.

It is certified that error appears in the above-identified patent and that said Letters Patent is hereby corrected as shown below:

Title page,
Item [56], References Cited, OTHER PUBLICATIONS, "Spiegel" reference, please delete "484" and insert therefor -- 1484 --;
"Van Veldhoven" reference, please delete "487" and insert therefor -- 1487 --.

Signed and Sealed this

Twenty-fifth Day of October, 2005

JON W. DUDAS
*Director of the United States Patent and Trademark Office*